US009890430B2

(12) United States Patent
Ellis et al.

(10) Patent No.: US 9,890,430 B2
(45) Date of Patent: Feb. 13, 2018

(54) COPY NUMBER ABERRATION DRIVEN ENDOCRINE RESPONSE GENE SIGNATURE

(71) Applicant: Washington University, Saint Louis, MO (US)

(72) Inventors: Matthew Ellis, Houston, TX (US); Jingqin Luo, Saint Louis, MO (US)

(73) Assignee: Washington University, St. Louis, MO (US)

( * ) Notice: Subject to any disclaimer, the term of this patent is extended or adjusted under 35 U.S.C. 154(b) by 322 days.

(21) Appl. No.: 14/407,913

(22) PCT Filed: Jun. 12, 2013

(86) PCT No.: PCT/US2013/045525
§ 371 (c)(1),
(2) Date: Dec. 12, 2014

(87) PCT Pub. No.: WO2013/188600
PCT Pub. Date: Dec. 19, 2013

(65) Prior Publication Data
US 2015/0240312 A1    Aug. 27, 2015

Related U.S. Application Data

(60) Provisional application No. 61/658,517, filed on Jun. 12, 2012.

(51) Int. Cl.
*G06F 19/20* (2011.01)
*C12Q 1/68* (2006.01)
(Continued)

(52) U.S. Cl.
CPC ........ *C12Q 1/6886* (2013.01); *B01J 19/0046* (2013.01); *G01N 33/57415* (2013.01);
(Continued)

(58) Field of Classification Search
None
See application file for complete search history.

(56) References Cited

U.S. PATENT DOCUMENTS 7,504,214 B2    3/2009    Erlander et al.
7,569,345 B2    8/2009    Cobleigh et al.
(Continued)

FOREIGN PATENT DOCUMENTS

WO    2011120984 A1    10/2011

OTHER PUBLICATIONS

M Dowsett et al. Meta-Analysis of Breast Cancer Outcomes in Adjuvant Trials of Aromatase Inhibitors Versus Tamoxifen. Journal of Clinical Oncology, Jan. 2010, vol. 28, No. 3, p. 509-518.*
(Continued)

*Primary Examiner* — John S. Brusca
*Assistant Examiner* — Olivia M Wise

(57) ABSTRACT

Disclosed are methods of predicting the likelihood of long-term survival without recurrence of breast cancer for a subject having estrogen receptor-positive (ER+) breast cancer treated with adjuvant endocrine monotherapy. In various embodiments, these methods comprise performing a gene expression profile of a breast tissue sample of substantially all of the genes of the "CADER set" described herein; calculating a risk score using a regression model; and applying a double median cutoff classification to assign the subject to a sensitive, indeterminate or resistant group, wherein assignment to a sensitive group predicts longer relapse-free survival compared to the median relapse-free survival of ER+ breast cancer patients treated with adjuvant endocrine monotherapy.

11 Claims, 5 Drawing Sheets

X-axis: resistant gene centroid
Y-axis: sensitive gene centroid

(51) Int. Cl.
G01N 33/574 (2006.01)
B01J 19/00 (2006.01)
G06F 19/24 (2011.01)
G06F 19/00 (2011.01)

(52) U.S. Cl.
CPC .............. *G06F 19/20* (2013.01); *G06F 19/24* (2013.01); *G06F 19/345* (2013.01); *C12Q 2600/112* (2013.01); *C12Q 2600/118* (2013.01); *C12Q 2600/158* (2013.01); *C12Q 2600/16* (2013.01); *G01N 2800/52* (2013.01); *G01N 2800/60* (2013.01)

(56) References Cited

U.S. PATENT DOCUMENTS

| | | |
|---|---|---|
| 2007/0059720 A9 | 3/2007 | Fuqua et al. |
| 2008/0014579 A1 | 1/2008 | Liu et al. |
| 2008/0032293 A1 | 2/2008 | Szabo |
| 2009/0215033 A1 | 8/2009 | Khan et al. |
| 2011/0014191 A1 | 1/2011 | Bertucci et al. |
| 2011/0130296 A1 | 6/2011 | Benz et al. |
| 2011/0145176 A1 | 6/2011 | Perou et al. |
| 2011/0152113 A1* | 6/2011 | Escudero ............. C12Q 1/6886 506/9 |
| 2011/0230360 A1 | 9/2011 | Stephan et al. |

OTHER PUBLICATIONS

La Korde et al. Gene expression pathway analysis to predict response to neoadjuvant docetaxel and capecitabine for breast cancer . Breast Cancer Res Treat 2010, vol. 119, p. 685-699 (Year: 2010).*
Affymetrix HG-U133 Plus 2.0 Array Search Results. Sep. 19, 2017, www.affymetrix.com, pp. 1-8.*
AGO2 GeneCard Entry.Sep. 19, 2017, www.genecards.org, pp. 1-17; newly cited.*
RRNAD1 GeneCard Entry. RRNAD1 (Sep. 19, 2017; www.genecards.org, pp. 1-14; newly cited).*
Chanrion, M., et al., A gene expression signature that can predict the recurrence of tamoxifen-treated primary breast cancer., Clin Cancer Res, 14(6), 1744-1752 (2008).
Cheang, M.C.U., et al., Ki67 Index, HER2 Status, and Prognosis of Patients With Luminal B Breast Cancer., J. Natl. Cancer Inst., 101(10): 736-750 (2009).
Galanina, N., et al., Molecular Predictors of Response to Therapy for Breast Cancer., Cancer J., 17(2), 96-103 (Mar./Apr. 2011).
Loi, S., et al., Definition of clinically distinct molecular subtypes in estrogen receptor-positive breast carcinomas through genomic grade., J. Clin. Oncol., 25(10), 1239-1246 (Apr. 2007).
Nielsen, T.O., et al., A comparison of PAM50 intrinsic subtyping with immunohistochemistry and clinical prognostic factors in tamoxifen-treated estrogen receptor-positive breast cancer., Clin. Cancer Res., 16(21), 5222-5232 (Nov. 2010).
Olson, J.A. Jr., et al. Improved surgical outcomes for breast cancer patients receiving neoadjuvant aromatase inhibitor therapy: results from a multicenter phase II trial., J. Am. Coll. Surg., 208(5), 906-914 (2009).
Paik, S., et al., A multigene assay to predict recurrence of tamoxifen-treated, node-negative breast cancer., N. Engl. J. Med., 351(27), 2817-2826 (Dec. 2004).
Parker, J.S., et al., Supervised risk predictor of breast cancer based on intrinsic subtypes., J. Clin. Oncol., 27(8), 1160-1167 (Mar. 2009).
Pawitan, Y., et al., Gene expression profiling spares early breast cancer patients from adjuvant therapy: derived and validated in two population-based cohorts., Breast Cancer Res., 7(6), R953-R964 (Oct. 2005).
Ringner M., et al., GOBO: gene expression-based outcome for breast cancer online PLOS ONE, 6(3), E17911 (Mar. 2011).
Rupp, G. and Locker, J., 395, Lab Invest., 56(1),A67 (Mar. 1987).
Schena, M., et al., A two-subunit type I DNA topoisomerase (reverse gyrase) from an extreme hyperthermophile., Proc. Natl. Acad. Sci. USA, 93(2),106-149 (Oct. 1996).
Sørlie T. et al., Gene expression patterns of breast carcinomas distinguish tumor subclasses with clinical implications., Proc. Natl. Acad. Sci. USA, 98(19), 10869-10874 (Sep. 2001).
Symmans, W.F., et al., Genomic index of sensitivity to endocrine therapy for breast cancer., J. Clin. Oncol. 28(27), 4111-4119 (Sep. 2010).
Van Tine, B.A., et al., ER and PI3K independently modulate endocrine resistance in ER positive breast cancer., Cancer Discov., 1, 287-288 (2011).
Van De Vijver, M.J., et al., A gene-expression signature as a predictor of survival in breast cancer., N. Engl. J. Med., 347(25), 1999-2009 (Dec. 2002).
Velculescu, V.E., et al., Serial analysis of gene expression., Science 270(5235), 484-487 (Oct. 1995).
Velculescu, V.E., et al., Characterization of the yeast transcriptome., Cell 88, 243-51 (Jan. 1997).
Wang, Y., et al., Gene-expression profiles to predict distant metastasis of lymph-node-negative primary breast cancer., Lancet 365, 671-679 (Feb. 2005).
Zhang, Y., et al., The 76-gene signature defines high-risk patients that benefit from adjuvant tamoxifen therapy., Breast Cancer Res. Treat., 116, 303-309 (2009).

* cited by examiner

X-axis: resistant gene centroid
Y-axis: sensitive gene centroid

COPY NUMBER ABERRATION DRIVEN ENDOCRINE RESPONSE GENE SIGNATURE

CROSS REFERENCE TO RELATED APPLICATION

This application claims priority from U.S. Provisional Application Ser. No. 61/658,517 filed Jun. 12, 2012, which is incorporated herein by reference in its entirety.

STATEMENT REGARDING FEDERALLY SPONSORED RESEARCH

This invention was made with government support under CA114722, CA095614, and CA068438 awarded by the National Institutes of Health. The government has certain rights in the invention.

FIELD

This work relates generally to breast cancer and, more particularly, to clinically useful methods and devices for assessing breast cancer prognosis.

INTRODUCTION

Genomic models based upon gene-expression signatures can provide clinically useful information for patient management. Nevertheless, patients are often assigned to intermediate risk groups in which the clinical decisions cannot be made confidently (Paik, S., et al. N. Engl. J. Med. 351:2817-26, 2004; Nielsen, T. O., et al. Clin. Cancer Res. 16:5222-32, 2010). Furthermore, besides HER2 and ER, most genes in these signatures are not amplicon-driven.

There are multiple studies that use gene expression markers for diagnosis, prognosis, determining treatment options, and monitoring relapse free survival.

Cobleigh et al., U.S. Pat. No. 7,569,345 ('345) provides a gene set for diagnosis and/or prognosis of breast cancer. This patent discloses a method of predicting the likelihood of long-term survival without recurrence of breast cancer for a patient having ER-positive breast cancer.

Bertucci et al., US Patent Application No. US 2011/0014191, discloses 16 serine/threonine kinases for determining poor clinical outcome or increased risk of recurrence following treatment when these genes are overexpressed.

Fuqua et al., US Patent Application No. US 2007/0059720, discloses RNA profiling for predicting resistance to chemotherapy in breast cancer.

Erlander et al., U.S. Pat. No. 7,504,214 ('214), discloses a gene signature of 149 genes that predicts tamoxifen treatment outcome in ER-positive breast cancer.

Perou et al., US Patent Application No. US 2011/0145176 ("Perou") discloses methods for classifying and evaluating the prognosis of a subject having breast cancer. Perou further provides methods for predicting outcome or response to therapy of a subject diagnosed with breast cancer using the PAM50 classification model.

Some of these tests are used in a clinical setting such as OncotypeDx Assay (Genomic Health, Inc.) and PAM50 assay (University Genomics, St. Louis, Mo.). OncotypeDx predicts recurrence of tamoxifen-treated, node-negative breast cancer (Paik, S., et al. N. Engl. J. Med. 351:2817-26, 2004), while PAM50 assay predicts variable response to chemotherapy (Parker, J. S., et al. J. Clin. Oncol. 27:1160-7, 2009).

While these studies predict and provide clinically useful information in certain groups of subjects, they are still limited in their ability to predict risk of relapse, i.e., many patients will be deemed to be of indeterminate risk of relapse using existing prognostic models. Thus, there is a need for methods for assigning greater percentages of subjects to either high risk of relapse or low risk of relapse in view of present prognostic models or methods that further dissect intermediate risk of relapse deemed by an existing model, for example, PAM50.

SUMMARY

Accordingly, the present inventors have succeeded in integrating gene expression and gene copy data in estrogen receptor positive (ER+) breast cancer to develop a new prognostic model that is superior to models derived from gene expression data alone. The mRNA expression from genes that are both prognostic in ER+ disease and modulated by copy number aberration (CNA) provide superior assay performance as well as new biological and clinical insights.

Thus, the present teachings are drawn to methods to determine relapse risk in a human subject afflicted with estrogen receptor-positive breast cancer treated with adjuvant endocrine monotherapy. In various embodiments, the methods comprise obtaining a breast cancer tissue sample from a human subject, determining gene expression levels in the sample of most, substantially all, or all the genes listed in the Copy number Aberration Driven Endocrine Response (CADER) set. The CADER set comprises, consists essentially of or consists of 27 treatment sensitivity genes and 27 treatment resistant genes listed in Table 1. The endocrine therapy sensitivity genes include PARP3, AZGP1, ZNF18, EPHX2, IGFBP4, NUDT18, FM05, C1orf66, COL14A1, PLAT, PCM1, PHYHD1, ZBTB20, NFKB1, TK2, ABAT, ACP6, TSPAN7, TNFRSF10B, GSTM1, CHDH, KCTD9, EVL, MAP2K4, RPL21 and STC2 and the endocrine therapy resistance genes include VDAC2, KIFC1, EIF2S2, EIF2C2, CCNB1, RAD54B, RACGAP1, CDC2, CDCA5, BIRC5, C8orf76, MCM10, TDG, UBE2C, TPX2, C20orf24, FBXO45, KIF4A, NUP107, DSC2, KIF18A, ZWINT, TMPO, CCT6A, TOP2A, CENPE and XPOT. The methods further comprise scaling the expression levels to have similar distribution of a matching prototype dataset and assigning the subject to a risk group for relapse based on the measured gene expression values. In various embodiments of the present teachings, a subject can be deemed to be at low risk of relapse if the subject has an up-regulated sensitive gene centroid value (relative to median zero) and a down-regulated resistant gene centroid value. In addition, in various embodiments, the subject can be deemed to be at high risk of relapse if the subject has a down-regulated sensitive gene centroid value (relative to median zero) and an up-regulated resistant gene centroid value. In various embodiments, a subject having an expression profile that does not lead to a determination of either low risk of relapse or high risk of relapse can be deemed to be at indeterminate risk of relapse.

In various embodiments, assigning the subject to a sensitive, indeterminate or resistant group comprises representing the expression levels as a coordinate in a quadrant in a 1-dimensional space by the resistant gene centroid and the sensitive gene centroid, and determining the Euclidean distance of the expression levels to the gene centroid of each of sensitive, resistant and indeterminate response groups, wherein the subject is assigned to the group with the shortest distance.

In some embodiments, determining the gene centroid of the treatment-resistant endocrine-response modifier genes and the gene centroid of the treatment-sensitive endocrine-response modifier genes can include calculating the double median cutoff classification scheme to categorize the risk score. In some embodiments, determining the gene centroid of the treatment-resistant endocrine-response modifier genes and the gene centroid of the treatment-sensitive endocrine-response modifier genes can comprise calculating the average of the expression levels of treatment-resistant genes and treatment-sensitive genes separately, and comparing them to the median zero (if genes are each median-centered) to give the risk score response categories.

In various embodiments, the adjuvant endocrine monotherapy can be tamoxifen treatment. In some embodiments, the adjuvant endocrine monotherapy can be aromatase inhibitor treatment.

In various embodiments, the CADER gene set can be significantly associated with copy number aberration. In some embodiments, a copy number aberration can be a copy number loss. In other embodiments, a copy number aberration can be a copy number gain, such as, in non-limiting example, a tandem duplication. In other embodiments, the copy number aberration can be copy number amplification.

Various embodiments of the present teachings include a microarray comprising, consisting essentially of, or consisting of a solid support and probe sets for each gene of the CADER set. In some configurations, the solid support can be, in non-limiting example, an Agilent 4*44 K platform (Agilent Technologies, Inc., Santa Clara Calif.) or a NanoString nCounter platform (NanoString Technologies, Inc., Seattle, Wash.). In some configurations, the probe sets can comprise, consist of or consist essentially of probes for each gene of the CADER set. In some configurations, the probe sets can comprise, consist essentially of, or consist of probes for each gene of the CADER set, plus probe sets for one or more housekeeping genes. In various embodiments, a microarray consisting essentially of a solid support and probe sets for each gene of the CADER set can also include additional probes and probe sets such as positive and negative controls, as well as proteins, buffers and salts that may be needed to conduct sample analysis.

In various embodiments, the present teachings include a microarray-based methods of predicting the likelihood of long-term survival without recurrence of cancer for a subject having estrogen receptor-positive breast cancer treated with endocrine monotherapy. The methods comprise obtaining a breast cancer tissue sample from a human subject, determining gene expression levels in the sample of most, substantially all, or all the genes listed in the CADER set. The CADER set comprises, consists essentially of or consists of 27 treatment sensitivity genes and 27 treatment resistant genes listed in Table 1. The endocrine therapy sensitivity genes include PARP3, AZGP1, ZNF18, EPHX2, IGFBP4, NUDT18, FMO5, C1orf66, COL14A1, PLAT, PCM1, PHYHD1, ZBTB20, NFKB1, TK2, ABAT, ACP6, TSPAN7, TNFRSF10B, GSTM1, CHDH, KCTD9, EVL, MAP2K4, RPL21 and STC2 and the endocrine therapy resistance genes include VDAC2, KIFC1, EIF2S2, EIF2C2, CCNB1, RAD54B, RACGAP1, CDC2, CDCA5, BIRC5, C8orf76, MCM10, TDG, UBE2C, TPX2, C20orf24, FBXO45, KIF4A, NUP107, DSC2, KIF18A, ZWINT, TMPO, CCT6A, TOP2A, CENPE and XPOT. The methods further comprise scaling the expression levels to have similar distribution of a matching prototype dataset and assigning the subject to a risk group for relapse based on the measured gene expression values. In various embodiments of the present teachings, a subject can be deemed to be at low risk of relapse if the subject has an up-regulated sensitive gene centroid value (relative to median zero) and a down-regulated resistant gene centroid value. In addition, in various embodiments, the subject can be deemed to be at high risk of relapse if the subject has a down-regulated sensitive gene centroid value (relative to median zero) and an up-regulated resistant gene centroid value. In various embodiments, a subject having an expression profile that does not lead to a determination of either low risk of relapse or high risk of relapse can be deemed to be at indeterminate risk of relapse.

In some embodiments, determining the gene centroid of the treatment-resistant endocrine-response modifier genes and the gene centroid of the treatment-sensitive endocrine-response modifier genes can include calculating the double median cutoff classification scheme to categorize the risk score. In some embodiments, determining the gene centroid of the treatment-resistant endocrine-response modifier genes and the gene centroid of the treatment-sensitive endocrine-response modifier genes can comprise calculating the average of the expression levels of treatment-resistant genes and treatment-sensitive genes separately, and comparing them to the median zero (if genes are each median-centered) to give the risk score response categories.

In various embodiments, the adjuvant endocrine monotherapy can be tamoxifen treatment. In some embodiments, the adjuvant endocrine monotherapy can be aromatase inhibitor treatment.

DETAILED DESCRIPTION

Figure 1:
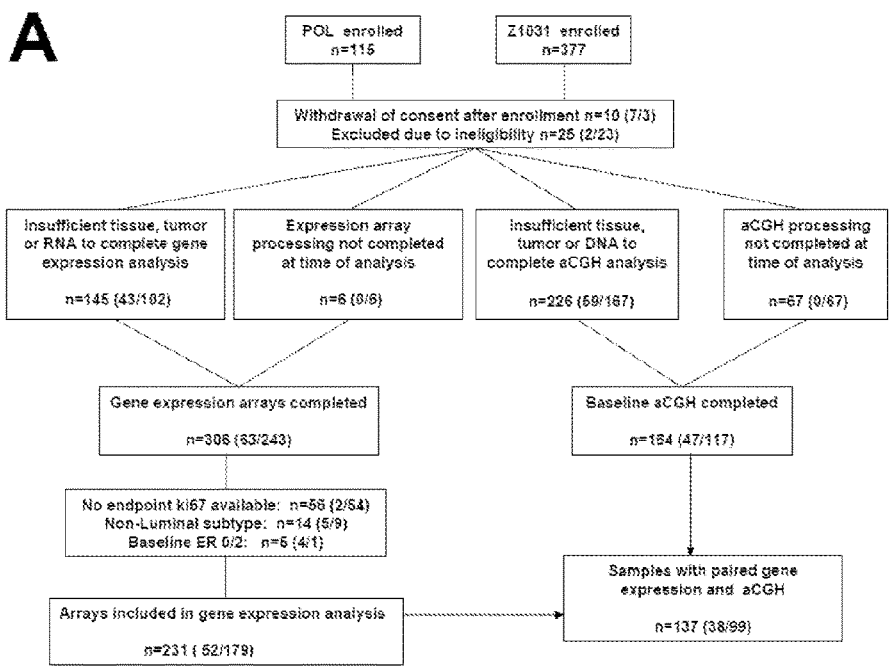
FIG. 1A-1B illustrate the combined remark diagram for the POL and Z1031 cohort (A) and analysis steps flow chart (B).
Figure 1:
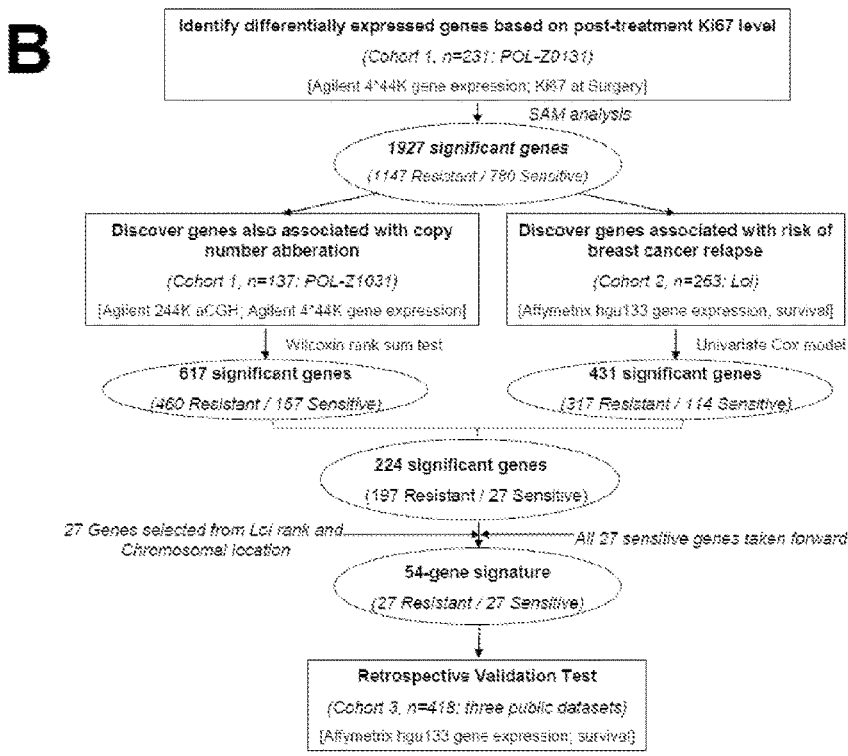

The present inventors disclose putative endocrine-response-modifier genes (ERMGs) that were identified by statistical associations between mRNA expression, copy number aberrations (CNA) and the anti-proliferative effects of neoadjuvant aromatase inhibitor (AI) therapy. Twenty-seven "treatment-sensitivity" and 27 "treatment-resistance" ERMGs were further selected through association with relapse-free survival (RFS) in patients uniformly treated with adjuvant tamoxifen monotherapy. The present teachings include 54 ERMGs and the derived copy number aberration driven endocrine response signature (CADER) that were further validated in three independent public datasets and compared with an established prognostic model (PAM50 ROR subtype-based score).

Unless defined otherwise, technical and scientific terms used herein have the same meaning as commonly understood by one of ordinary skill in the art to which the present teachings belong. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide a person of skill in the art with general guides to many of the terms used in the present application.

One skilled in the art will recognize many methods and materials similar or equivalent to those described herein, which could be used in the practice of the present teachings. The present teachings are in no way limited to the methods and materials described. For purposes of the present teachings, the following terms are defined below.

As used herein, "microarray" refers to an ordered arrangement of hybridizable array elements such as polynucleotide probes, on a substrate.

As used herein, "treatment sensitive genes" are genes that are up-regulated in patients who are sensitive to endocrine treatment.

As used herein, "treatment resistance genes" are genes that are up-regulated in patients who are resistant to endocrine treatment.

As used herein, "gene amplification" refers to abnormal multiple copies of a gene or gene fragment comprised by a cell or cell line.

As used herein, "amplicon" refers to an amplified stretch of DNA.

As used herein, "prediction" refers to the likelihood that a subject will respond either favorably or unfavorably to a drug or set of drugs, and also the extent of those responses, or that a patient will survive, following surgical removal or the primary tumor and/or chemotherapy for a certain period of time without cancer recurrence.

As used herein, "long-term" survival means survival for at least 5 years following surgery or other treatment.

As used herein, "tumor" refers to cancerous tumors.

As used herein, "pathology" of cancer refers to phenomena that compromise the health of a cancer patient. These include, without limitation, abnormal cell growth, metastasis, interference with the normal functioning of neighboring cells, release of cytokines or other secretory products at abnormal levels, suppression or aggravation of inflammatory or immunological responses, neoplasia, premalignancy, malignancy, and invasion of surrounding or distant tissues or organs.

As used herein, "biological sample" is any sampling of cells, tissues, or bodily fluids containing cells. Examples of biological samples include, but are not limited to, biopsies, smears, and bodily fluids such as blood, lymph, urine, saliva, nipple aspirates, and gynecological fluids.

As used herein, "blood" includes whole blood, plasma, and serum.

Methods and compositions described herein utilize laboratory techniques well known to skilled artisans. Such techniques can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Methods in Enzymology (Academic Press, Inc.); Handbook of Experimental Immunology, 4th edition (D. M. Weir & C. C. Blackwell, eds., Blackwell Science Inc., 1987); Current Protocols in Molecular Biology (F. M. Ausubel et al., eds., 1987); and PCR: The Polymerase Chain Reaction, (Mullis et al., eds., 1994).

Gene Expression Profiling

In general, methods of gene expression profiling can be divided into two large groups: methods based on hybridization analysis of polynucleotides, and methods based on sequencing of polynucleotides. Methods known in the art for the quantification of mRNA expression in a sample include northern blotting and in situ hybridization (Parker & Barnes, Methods in Molecular Biology 106:247-283 (1999)); RNAse protection assays (Hod, Biotechniques 13:852-854 (1992)); and reverse transcription-polymerase chain reaction (RT-PCR) (Weis et al., Trends in Genetics 8:263-264 (1992)). Alternatively, antibodies can be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). For example, RT-PCR can be used to compare mRNA levels in different sample populations, in normal and tumor tissues, with or without drug treatment, to characterize patterns of gene expression, to discriminate between closely related mRNAs, and/or to analyze RNA structure.

A first step for an RT-PCR analysis can be extraction and/or isolation of mRNA from a sample. In some embodiments, starting material can be total RNA isolated from a human tumor, a tumor cell line, and/or corresponding normal tissues or cell lines. RNA can be isolated from a variety of primary tumors, such as, without limitation, breast, lung, colon, prostate, brain, liver, kidney, pancreas, spleen, thymus, testis, ovary, uterus, etc., tumor, or tumor cell lines. If the source of mRNA is a primary tumor, mRNA can be extracted, for example, from frozen or archived paraffin-embedded and fixed (e.g. formalin-fixed) tissue samples.

Methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., BioTechniques 18:42044 (1995). In particular, RNA isolation can be performed using a purification kit, buffer set and protease from commercial manufacturers, such as Qiagen, according to the manufacturer's instructions. For example, total RNA from cells in culture can be isolated using Qiagen RNeasy® mini-columns. Other commercially available RNA isolation kits include Master-Pure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from a tumor can be isolated, for example, by cesium chloride density gradient centrifugation.

A first step in gene expression profiling by RT-PCR can be the reverse transcription of the RNA template into cDNA, followed by amplification in a PCR reaction. For example, extracted RNA can be reverse-transcribed using a GeneAmp RNA PCR kit (Perkin Elmer, Calif., USA), following the manufacturer's instructions. The cDNA can then be used as template in a subsequent PCR amplification and quantitative analysis using, for example, a TaqMan® (Life Technologies, Inc., Grand Island, N.Y.) assay.

TaqMan® RT-PCR can be performed using commercially available equipment, such as, for example, an ABI PRISM 7700™ Sequence Detection System™ (Perkin-Elmer-Applied Biosystems, Foster City, Calif., USA), or Lightcycler (Roche Molecular Biochemicals, Mannheim, Germany). RT-PCR can be performed using an internal standard such as mRNA for glyceraldehyde-3-phosphate-dehydrogenase (GAPDH) and/or β-actin as a control (see, e.g., Held et al., Genome Research 6: 986-994, 1996).

Representative protocols for profiling gene expression using fixed, paraffin-embedded tissues as the RNA source, including mRNA isolation, purification, primer extension and amplification are given in various published journal articles (for example: T. E. Godfrey et al., J. Molec. Diagnostics 2: 84-91, 2000; K. Specht et al., Am. J. Pathol. 158: 419-429, 2001). In various configurations, a representative process can start with cutting about 10 µm-thick sections of paraffin-embedded tumor tissue samples. The RNA can be extracted, and protein and DNA can be removed. RNA repair and/or amplification steps can be included.

In some aspects of the present teachings, PCR primers and probes can be designed based upon intron sequences present in the gene to be amplified. In such aspects, a first step in the primer/probe design can be the delineation of intron sequences within the genes. This can be accomplished using publicly available software, such as the DNA BLAST software (Kent, W. J., Genome Res. 12(4): 656-664, 2002). Subsequent steps can follow well established methods of PCR primer and probe design.

In some configurations, in order to avoid non-specific signals, repetitive sequences within the introns can be masked when designing the primers and probes. This can be accomplished by using software such as the Repeat Masker program available on-line through the Baylor College of Medicine. This program can be used to screen DNA sequences against a library of repetitive elements and returns a query sequence in which the repetitive elements are masked. The masked intron sequences can then be used to design primer and probe sequences using a commercially or otherwise publicly available primer/probe design package, such as Primer Express (Applied Biosystems); MGB assay-by-design (Applied Biosystems); Primer3 (Steve Rozen and Helen J. Skaletsky (2000) Primer3 on the WWW for general users and for biologist programmers. In: Krawetz S, Misener S (eds) Bioinformatics Methods and Protocols: Methods in Molecular Biology. Humana Press, Totowa, N.J., pp 365-386).

Factors considered in PCR primer design include primer length, melting temperature (Tm), and G/C content, specificity, complementary primer sequences, and 3'-end sequence. In general, optimal PCR primers are generally 17-30 bases in length, and contain about 20% from 10% to 80%, or about 80% G+ C bases, such as, for example, about 50%, from 50 to 60%, or about 60% G+C bases. In various configurations, Tm's between 50 and 80° C., e.g. about 50 to 70° C. can be preferred.

Further guidelines for PCR primer and probe design can be found in various published sources, e.g. Dieffenbach, C. W. et al., "General Concepts for PCR Primer Design" in: PCR Primer, A Laboratory Manual, Cold Spring Harbor Laboratory Press, New York, 1995, pp. 133-155; Innis and Gelfand, "Optimization of PCRs" in: PCR Protocols, A Guide to Methods and Applications, CRC Press, London, 1994, pp. 5-11; and Plasterer, T. N. Primerselect: Primer and probe design. Methods Mol. Biol. 70:520-527 (1997), the entire disclosures of which are hereby expressly incorporated by reference.

Microarrays

In some embodiments, differential gene expression can also be identified, or confirmed using a microarray technique. Thus, the expression profile of breast cancer-associated genes can be measured in either fresh or paraffin-embedded tumor tissue, using microarray technology. In these methods, polynucleotide sequences of interest (including cDNAs and oligonucleotides) can be plated, or arrayed, on a microchip substrate. The arrayed sequences are then hybridized with specific DNA probes from cells or tissues of interest. Just as in the RT-PCR method, the source of mRNA typically can be total RNA isolated from human tumors or tumor cell lines, and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue samples.

In an embodiment of the microarray technique, PCR-amplified inserts of cDNA clones can be applied to a substrate in a dense array. The microarrayed genes, immobilized on the microchip, can be suitable for hybridization under stringent conditions.

In some embodiments, fluorescently labeled cDNA probes can be generated through incorporation of fluorescent nucleotides by reverse transcription of RNA extracted from tissues of interest. Labeled cDNA probes applied to the chip can hybridize with specificity to loci of DNA on the array. After washing to remove non-specifically bound probes, the chip can be scanned by confocal laser microscopy or by another detection method, such as a CCD camera. Quantification of hybridization of each arrayed element allows for assessment of corresponding mRNA abundance.

In some configurations, dual color fluorescence can be used. With dual color fluorescence, separately labeled cDNA probes generated from two sources of RNA are hybridized pairwise to the array. The relative abundance of the transcripts from the two sources corresponding to each specified gene is thus determined simultaneously. In various configurations, the miniaturized scale of the hybridization can afford a convenient and rapid evaluation of the expression pattern for large numbers of genes. In various configurations, such methods can have sensitivity required to detect rare transcripts, which are expressed at fewer than 1000, fewer than 100, or fewer than 10 copies per cell. In various configurations, such methods can detect at least approximately two-fold differences in expression levels (Schena et al., Proc. Natl. Acad. Sci. USA 93(2): 106-149 (1996)). In various configurations, microarray analysis can be performed by commercially available equipment, following manufacturer's protocols, such as by using the Affymetrix GenChip technology, or Incyte's microarray technology.

Serial Analysis of Gene Expression (SAGE)

SAGE is a method that allows simultaneous and quantitative analysis of a large number of gene transcripts, without the need of providing an individual hybridization probe for each transcript, hi various configurations of these methods, a short sequence tag (about 10-14 bp) is generated that contains sufficient information to uniquely identify a transcript, provided that the tag is obtained from a unique position within each transcript. Then, many transcripts are linked together to form long serial molecules that can be sequenced, revealing the identity of the multiple tags simultaneously. The expression pattern of any population of transcripts can be quantitatively evaluated by determining the abundance of individual tags, and identifying the gene corresponding to each tag (Velculescu et al., Science 270: 484-487 (1995); Velculescu et al., Cell 88:243-51 (1997).

MassARRAY Technology

The MassARRAY (Sequenom, San Diego, Calif.) technology is an automated, high-throughput method of gene expression analysis using mass spectrometry (MS) for detection. According to this method, following the isolation of RNA, reverse transcription and PCR amplification, the cDNAs are subjected to primer extension. The cDNA-derived primer extension products are purified, and dispensed on a chip array that is pre-loaded with the components needed for MALTI-TOF MS sample preparation. The various cDNAs present in the reaction are quantitated by analyzing the peak areas in the mass spectrum obtained.

Gene Expression Analysis by Massively Parallel Signature Sequencing (MPSS)

This method, described by Brenner et al., Nature Biotechnology 18:630-634 (2000), is a sequencing approach that combines non-gel-based signature sequencing with in vitro cloning of millions of templates on separate 5 µm diameter microbeads. First, a microbead library of DNA templates is constructed by in vitro cloning. This is followed by the assembly of a planar array of the template-containing microbeads in a flow cell at a high density (typically greater than $3.\text{times}.10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

General Description of the mRNA Isolation, Purification and Amplification

The steps of a representative protocol for profiling gene expression using fixed, paraffin-embedded tissues as the RNA source, including mRNA isolation, purification, primer extension and amplification are given in various published journal articles {for example: T. E. Godfrey et al. J. Molec. Diagnostics 2: 84-91 [2000]; K. specht et al., Am. J. Pathol. 158: 419-29 [2001]}. Briefly, a representative process starts with cutting about 10 urn thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR. Finally, the data are analyzed to identify the best treatment option(s) available to the patient on the basis of the characteristic gene expression pattern identified in the tumor sample examined.

Breast Cancer Gene Set, Assayed Gene Subsequences, and Clinical Application of Gene Expression Data Some embodiments of the present teachings comprise measuring expression levels of certain genes by breast cancer tissue to provide prognostic information. In various configurations, expression levels can be normalized regarding both differences in the amount of RNA assayed and variability in the quality of the RNA used. Therefore, an assay can involve measurement of the expression of certain "normalizing" genes, including housekeeping genes such as, for example, GAPDH and/or Cyp1. In some configurations, normalization can be based on the mean or median signal (Ct) of all of the assayed genes or a subset thereof (global normalization approach). On a gene-by-gene basis, measured normalized amount of a patient tumor mRNA can be compared to the amount found in a breast cancer tissue reference set. The number (N) of breast cancer tissues in this reference set can be sufficiently high to ensure that different reference sets (as a whole) behave essentially the same way. In various configurations, if this condition is met, the identity of the individual breast cancer tissues present in a particular set can have no significant impact on the relative amounts of the genes assayed. In some configurations, the breast cancer tissue reference set can consist of or consist essentially of at least about 30, preferably at least about 40, more preferably at least about 50, different FPE breast cancer tissue specimens. Unless noted otherwise, normalized expression levels for each mRNA/tested tumor/patient can be expressed as a percentage of the expression level measured in the reference set. More specifically, the reference set of a sufficiently high number (e.g. at least 40) of tumors can yield a distribution of normalized levels of each mRNA species. The level measured in a particular tumor sample to be analyzed falls at some percentile within this range, which can be determined by methods well known in the art. Below, unless noted otherwise, reference to expression levels of a gene assume normalized expression relative to a reference set although unless stated otherwise.

In some embodiments, gene expression data can be pre-processed, by addressing for example but without limitation, missing data, translation, scaling, normalization, and/or weighting. In some configurations, multivariate projection methods, such as principal component analysis (PCA) and partial least squares analysis (PLS), can be used as scaling-sensitive methods. In these configurations, by using prior knowledge and experience about the type of data studied, the quality of the data prior to multivariate modeling can be enhanced by scaling and/or weighting. In some embodiments, scaling and weighting can be used to place the data in the correct metric, thereby revealing patterns inherent in the data.

In some configurations, missing data, for example gaps in column values, can be replaced or "filled" with, for example but without limitation, the mean value of a column ("mean fill"); a random value ("random fill"); or a value based on a principal component analysis ("principal component fill").

As used herein, "translation" of descriptor coordinate axes can include normalization and mean centering. In some configurations, "normalization" can be used to remove sample-to-sample variation. In various embodiments, for microarray data, the process of normalization can be used to remove systematic errors by balancing the fluorescence intensities of the two labeling dyes. In various configurations, methods for calculating normalization factor can include: (i) global normalization that uses all genes on the array; (ii) housekeeping genes normalization that uses constantly expressed housekeeping/invariant genes; and (iii) internal controls normalization that uses known amount of exogenous control genes added during hybridization (Quackenbush (2002) Nat. Genet. 32 (Suppl.), 496-501). In one embodiment, intrinsic genes disclosed herein can be normalized to control housekeeping genes. For example, the housekeeping genes described in U.S. Patent Publication 2008/0032293, which is herein incorporated by reference in its entirety, can be used for normalization. Exemplary housekeeping genes include MRPL19, PSMC4, SF3A1, PUM1, ACTB, GAPD, GUSB, RPLP0, and TFRC. It will be understood by one of skill in the art that the methods disclosed herein are not bound by normalization to any particular housekeeping genes, and that any suitable housekeeping gene(s) known in the art can be used.

A gene centroid represents the average expression levels of a set of predefined genes for an individual relative to control levels. The CADER classification centers on two centroids, the centroid of the 27 CADER resistant genes and the centroid of the 27 CADER sensitive genes.

In various configurations, many normalization approaches are possible, which can be applied at any of several points in the analysis. In a configuration, microarray data can be normalized using the LOWESS method (Yang, Y. H., et al. Nucleic Acids Res. 30:e15, 2002). In another embodiment, qPCR data can be normalized to the geometric mean of a set of housekeeping genes.

In some embodiments, "mean centering" can also be used to simplify interpretation. In these embodiments, for each descriptor, the average value of that descriptor for all samples can be subtracted. In this way, the mean of a descriptor coincides with the origin, and all descriptors can be "centered" at zero. In "unit variance scaling," data can be scaled to equal variance. In various configurations, the value of each descriptor can be scaled by 1/StDev, where StDev is the standard deviation for that descriptor for all samples.

In some embodiments, "Pareto scaling" can also be used to simplify interpretation (van den Berg, R. A., et al., BMC Genomics. 7:142, 2006). In pareto scaling, the value of each descriptor is scaled by 1/sqrt (StDev), where StDev is the standard deviation for that descriptor for all samples. In this way, each descriptor has a variance numerically equal to its initial standard deviation. In various configurations, pareto scaling can be performed, for example, on raw data or mean centered data.

In some embodiments, "logarithmic scaling" can be used to assist interpretation when data have a positive skew and/or when data spans a large range, e.g., several orders of magnitude. In these embodiments, a value is replaced by the logarithm of that value.

In some embodiments, "equal range scaling" can be used to assist interpretation. In these embodiments, each descriptor is divided by the range of that descriptor for all samples. In this way, all descriptors have the same range, that is, 0-1. However, this method can be sensitive to the presence of outlier points.

In some embodiments, "autoscaling," can be used to assist interpretation. In these embodiments, each data vector is mean centered and unit variance scaled. This technique can be used to weigh each descriptor equally.

Figure 4:
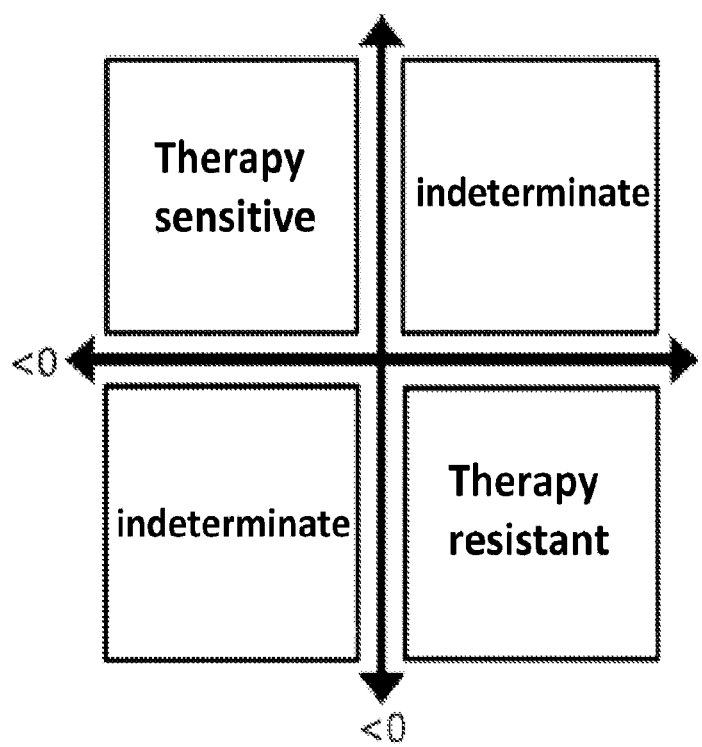
FIG. 4 illustrates a quadrant in a 2-dimensional space by the resistant and the sensitive gene centroid.

In various embodiments, a double median cut-off scheme can be used to classify subjects into the three response groups (sensitive, resistant and indeterminate). In various configurations, each gene can be normalized to have a zero median and a unit inter-quartile range (IQR). The gene centroid of 27 CADER resistant genes and the gene centroid of the 27 CADER sensitive genes can be separately calculated. Because of this normalization, the double median cut-off can be equivalent to double zero cut-off since all genes and centroids have a zero median. Patients with a greater-than-zero resistant gene centroid value and a less-than-zero sensitive gene centroid can be assigned into the therapy resistant group while the patients with less-than-zero resistant gene centroid value and a greater-than-zero sensitive gene centroid can be assigned into the therapy sensitive group. In various configurations, detection of up-regulation of resistant genes can lead to a bad prognosis, and detection of up-regulation of the sensitive genes can lead to good prognosis. The remaining patients can have indeterminate responses to therapy. (FIG. 4)

Methods

The methods and compositions described herein utilize laboratory techniques well known to skilled artisans, and can be found in references such as Sambrook and Russel (2006), Condensed Protocols from Molecular Cloning: A Laboratory Manual, Cold Spring Harbor Laboratory Press, ISBN 0879697717; Sambrook and Russel (2001) Molecular Cloning: A Laboratory Manual, Cold Spring Harbor Laboratory Press, ISBN 0879695773; Ausubel et al. (2002) Short Protocols in Molecular Biology, Current Protocols, ISBN 0471250929; Spector et al. (1998) Cells: A Laboratory Manual, Cold Spring Harbor Laboratory Press, ISBN 0879695226.

EXAMPLES

The present teachings including descriptions provided in the Examples that are not intended to limit the scope of any claim or aspect. Unless specifically presented in the past tense, an example can be a prophetic or an actual example. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Example 1

This example illustrates the identification of Endocrine Response Modifier Genes (ERMG).

Study samples to identify ERMG were used from previously described neoadjuvant endocrine therapy studies, pre-operative letrozole Phase 2 (POL) trial and ACOSOG Z1031 neoadjuvant aromatase inhibitor (AI) trial (Van Tine, B. A., et al. 2011; Olson, J.A., Jr., et al. 2009). A 10% Ki67 cut-point in the surgical specimen was used to define AI sensitivity and resistance, as this cut point is a reliable surrogate for relapse-free survival (RFS). Fifty-two and 179 patients from the POL and Z1031 cohort respectively were used for discovery (FIG. 1A). Total sample size (sample size for POL/sample size for Z1031) are noted in each box. Baseline PAM50 subtype and baseline and surgical specimen ER and Ki67 levels were similarly distributed between the two cohorts. Public gene expression data were accessed on 263 patients from the Loi study (Loi, S., et al. 2007, referred to herein as "Loi"), 195 from the Symmans study (Symmans, W. F., et al. 2010, referred to herein as "Symmans"), 136 from the Zhang study (Zhang, Y., et al. 2009, referred to herein as "Zhang") and 87 from the Pawitan study (Pawitan, Y., et al. 2005, referred to herein as "Pawitan"), restricting to ER+ breast cancer patients treated with adjuvant endocrine monotherapy (i.e. no chemotherapy) (FIG. 1B). Sequential analysis steps that lead to the CADER signature are shown in this flow chart (FIG. 1B). In each step, analyzed cohorts, analysis end points, genomic profiling and statistical methods, and number of retained treatment resistance and sensitivity signature genes are presented.

ERMGs were identified in study samples by significance analysis of microarrays (SAM) as genes differentially expressed between the sensitive and resistant tumors (defined by the 10% Ki67 cut point) at the 5% false discovery rate (FDR). There were 1927 putative ERMGs that fit these criteria. Of these, 1047 are up-regulated in the resistant tumors with a fold-change (relative to sensitive) ranging from 1.29~1.80 while 780 ERMGs were up-regulated in the sensitive tumors with a fold change (relative to resistant) between 1.32 and 1.81.

Two exercises were conducted in parallel to focus verification and validation efforts on the most relevant genes. First, genes were excluded whose mRNA levels were not significantly associated with CNA, based on 137 POL-Z1031 cases with paired gene-expression and aCGH, comparative genomic hybrid, data. This analysis revealed that 617 (460 resistant and 157 sensitive) of the original 1927 ERMGs were differentially expressed between copy number gain/amplification versus neutral/LOH samples. Correlation matrixes demonstrated that copy number data in contiguous chromosomal locations were highly correlated. Chromosomes (Chr) 6, 1, 20, 3 and 8 harbored the greatest number of CNA-associated resistance-ERMGs (n=64, 60, 43, 40, 40 respectively) while sensitivity-ERMGs were largely located on Chr17, 4, 1, 5, 11 and 8 (n=25, 18, 15, 14, 13, and 12 respectively), hi general, the sensitivity ERMGs were predominantly affected by LOH whereas resistance ERMGs were dominantly affected by gene gain and amplification (Table 1). Table 1 presents the list of the 54 ERMGs including official gene symbols, gene descriptions, Cox survival P-values from Loi, copy number P values are shown for each ERMG.

TABLE 1

Listing of the 54 ERMGs.

| Symbol | CNV Percentage (del/neutral/gain/amp) | Locus | CNV P | Cox P |
|---|---|---|---|---|
| Endocrine Therapy Sensitivity Genes | | | | |
| PARP3 | 36.1/60.6/3.2/— | 3p21.31 | 0.0418 | 1.80E−05 |
| AZGP1 | 31.2/58.4/10.4/— | 7q22.1 | 0.0013 | 3.81E−05 |
| ZNF18 | 54.2/44.5/1.3/— | 17p11.2 | 0.0416 | 1.13E−04 |
| EPHX2 | 48.0/40.9/11.0/— | 8p21 | 0.0004 | 6.57E−04 |
| IGFBP4 | 34.6/45.8/17.0/2.6 | 17q12 | 0.0239 | 0.0010 |
| NUDT18 | 53.6/36.6/9.8/— | 8p21.3 | 0.0003 | 0.0010 |
| FMO5$^C$ | 0.6/38.1/55.5/5.8 | 1q21.1 | 0.0008 | 0.0018 |
| C1orf66$^W$ | 2.6/34.8/57.4/5.2 | 1q23.1 | 2.68E−09 | 0.0021 |
| COL14A1 | 2.6/47.7/27.4/22.2 | 8q23 | 0.0003 | 0.0031 |
| PLAT | 16.2/50.6/22.7/10.4 | 8p12 | 0.0001 | 0.0033 |
| PCM1$^C$ | 43.2/45.8/10.3/0.6 | 8p22 | 1.8E−05 | 0.0051 |
| PHYHD1 | 44.0/52.0/4.0/— | 9q34.11 | 0.0013 | 0.0072 |
| ZBTB20 | 4.7/82.4/12.2/0.7 | 3q13.2 | 0.0344 | 0.0081 |
| NFKB1 | 6.5/84.5/8.4/0.6 | 4q24 | 0.0214 | 0.0081 |
| TK2 | 67.3/26.1/6.5/— | 16q22 | 0.0019 | 0.0081 |
| ABAT | 4.5/49.7/43.9/1.9 | 16p13.2 | 1.56E−05 | 0.0083 |
| ACP6 | 0.6/38.1/54.8/6.5 | 1q21 | 0.0023 | 0.0094 |
| TSPAN7 | 17.4/66.5/14.8/1.3 | Xp11.4 | 0.0482 | 0.0097 |
| TNFRSF10B | 50.3/40.6/9.0/— | 8p22 | 0.0004 | 0.0131 |
| GSTM1$^{PK}$ | 27.1/69.0/3.2/0.6 | 1p13.3 | 0.0245 | 0.0196 |
| CHDH | 23.4/73.4/3.2/— | 3p21.1 | 0.0115 | 0.0244 |
| OSBPL1A | 25.2/66.5/7.7/0.6 | 18q11.1 | 0.0423 | 0.0272 |
| KCTD9 | 45.8/43.9/10.3/— | 8p21.1 | 0.0051 | 0.0285 |
| EVL | 21.9/65.6/11.3/1.3 | 14q32.2 | 0.0001 | 0.0294 |
| MAP2K4 | 54.5/44.2/1.3/— | 17p11.2 | 0.0170 | 0.0308 |
| RPL21 | 27.7/61.9/8.4/1.9 | 13q12.2 | 0.0006 | 0.0333 |
| STC2$^C$ | 9.0/70.3/20.6/— | 5q35.1 | 0.0070 | 0.0466 |
| Endocrine Therapy Resistance Genes | | | | |
| VDAC2 | 5.2/78.7/14.2/1.9 | 10q22 | 3.2E−07 | 3.44E−08 |
| KIFC1 | 17.4/73.5/9.0/— | 6p21.3 | 0.0039 | 1.63E−06 |
| EIF2S2 | 11.1/63.4/25.5/— | 20q11.2 | 2.3E−04 | 3.57E−06 |
| EIF2C2 | 7.2/48.4/26.8/17.6 | 8q24 | 5.4E−14 | 4.80E−06 |
| CCNB1$^{PKP}$ | 24.5/58.1/17.4/— | 5q12 | 4.5E−04 | 7.55E−06 |
| RAD54B | 2.0/47.1/33.3/17.6 | 8q22.1 | 2.4E−15 | 1.12E−05 |
| RACGAP1 | 11.6/76.1/12.3/— | 12q13.12 | 0.0187 | 2.23E−05 |
| CDC2$^{C;\,P}$ | 5.2/80.0/14.2/0.6 | 10q21.1 | 0.0014 | 2.27E−05 |
| CDCA5 | 30.3/58.1/10.3/1.3 | 11q12.1 | 6.2E−04 | 2.29E−05 |
| BIRC5$^{PK;\,P}$ | 33.5/38.1/27.1/1.3 | 17q25 | 7.2E−07 | 2.67E−05 |
| C8orf76 | 5.8/46.1/28.6/19.5 | 8q24.13 | 1.4E−18 | 3.27E−05 |
| MCM10 | 9.7/78.1/11.0/1.3 | 10p13 | 1.2E−04 | 3.52E−05 |
| TDG | 11.0/72.9/15.5/0.6 | 12q24.1 | 1.4E−04 | 3.68E−05 |
| UBE2C$^{C;\,P}$ | 4.5/54.5/36.4/4.5 | 20q13.12 | 4.6E−04 | 3.70E−05 |
| TPX2 | 11.0/63.9/25.2/— | 20q11.2 | 7.0E−03 | 3.71E−05 |
| C20orf24 | 13.6/57.4/25.2/3.9 | 20q11.23 | 5.2E−08 | 4.45E−05 |
| FBXO45 | 13.6/70.3/14.8/1.3 | 3q29 | 3.6E−05 | 4.46E−05 |
| KIF4A | 22.2/69.9/7.8/— | Xq13.1 | 3.5E−02 | 4.51E−05 |
| NUP107 | 2.0/69.5/25.3/3.2 | 12q15 | 2.6E−07 | 6.62E−05 |
| DSC2 | 14.2/71.6/13.6/0.6 | 18q12.1 | 2.5E−02 | 6.91E−05 |
| KIF18A | 6.6/77.0/15.1/1.3 | 11p14.1 | 3.5E−07 | 7.09E−05 |
| ZWINT | 5.2/80.7/13.6/0.6 | 10q21 | 3.2E−02 | 7.24E−05 |
| TMPO | 12.6/68.9/17.2/1.3 | 12q22 | 1.0E−02 | 7.71E−05 |
| CCT6A | 14.2/69.7/16.1/— | 7p11.2 | 2.6E−04 | 8.91E−05 |
| TOP2A | 43.8/40.5/15.0/0.6 | 17q21 | 2.7E−07 | 9.03E−05 |
| CENPE | 6.5/85.2/7.7/0.6 | 4q24 | 1.9E−04 | 1.31E−04 |
| XPOT | 3.9/68.4/25.2/2.6 | 12q14.2 | 2.0E−03 | 1.32E−04 |

In the second exercise, the 1927 putative ERMGs were simultaneously screened for association with RFS using the independent Loi cohort (Loi, S., et al. 2007). In univariate survival analysis, a total of 431 ERMGs (317 resistant and 114 sensitive) were significantly associated with RFS in the same resistance/sensitivity direction (by hazard ratio estimation) as observed in POL-Z1031. Only fifty two of these genes (12%) overlapped with those contained in the five gene signatures previously published as prognostic in ER+ breast cancer (Paik, S., et al. N. Engl. J. Med. 351:2817-26, 2004; Nielsen, T. O., et al. Clin. Cancer. Res. 16:5222-32, 2010; Chanrion, M., et al. Clin. Cancer. Res. 14:1744-52, 2008; van de Vijver, M. J., et al. N. Engl. J. Med. 347:1999-2009, 2002; Wang, Y., et al. Lancet. 365:671-9, 2005). Taking the results from both exercises, two hundred and twenty four ERMGs (197 resistant and 27 sensitivity) survived.

Example 2

This example illustrates the prognostic power of the 54 ERMGs individually.

Three independent public microarray data sets on ER+ breast cancer tumors treated with adjuvant tamoxifen only were accessed (Symmans, Zhang and Pawitan). The hazard ratios (HRs), 95% CIs and P-values estimated from univariate Cox regression models were calculated for each ERMG within each public cohort. By meta-analysis, 25 among the 48 genes present in at least one cohort showed significant association with RFS and in the expected direction as from the discovery. Hierarchical cluster analyses on the 54 ERMGs subsequently demonstrated that the sensitivity and resistant genes separated consistently and cleanly in all cohorts. Based on the joint expression pattern of treatment sensitivity and resistance ERMGs, three groups of samples were definable: a group with high-expression of resistance-ERMGs and low-expression of sensitivity-ERMGs ('resistant' group), a second group with the opposite expression pattern ('sensitive' group) and a third with a mixed pattern ('indeterminate' group).

Figure 2:
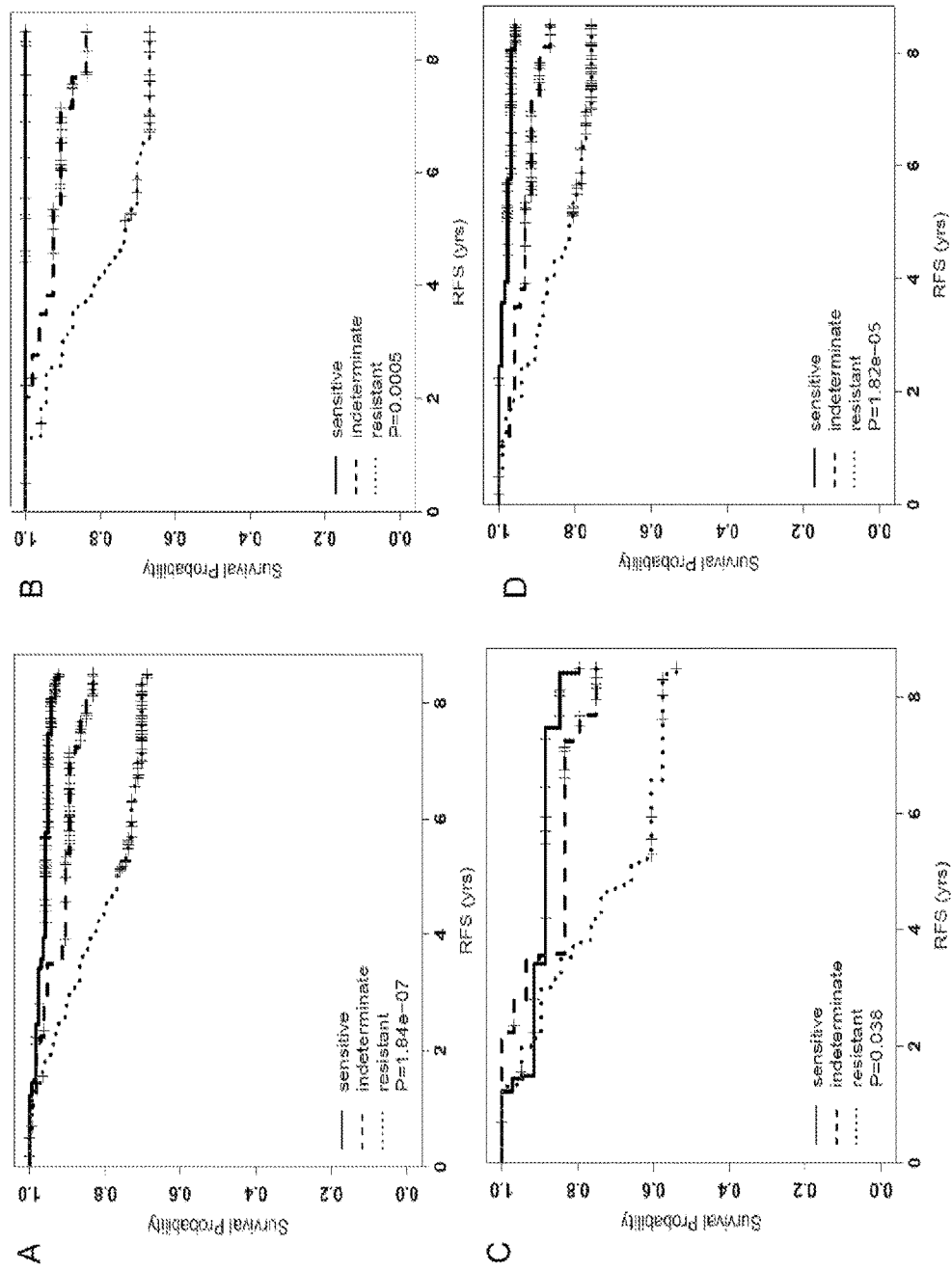
FIG. 2A-D illustrate Kaplan Meier (KM) curves of the CADER categories.
Figure 3:
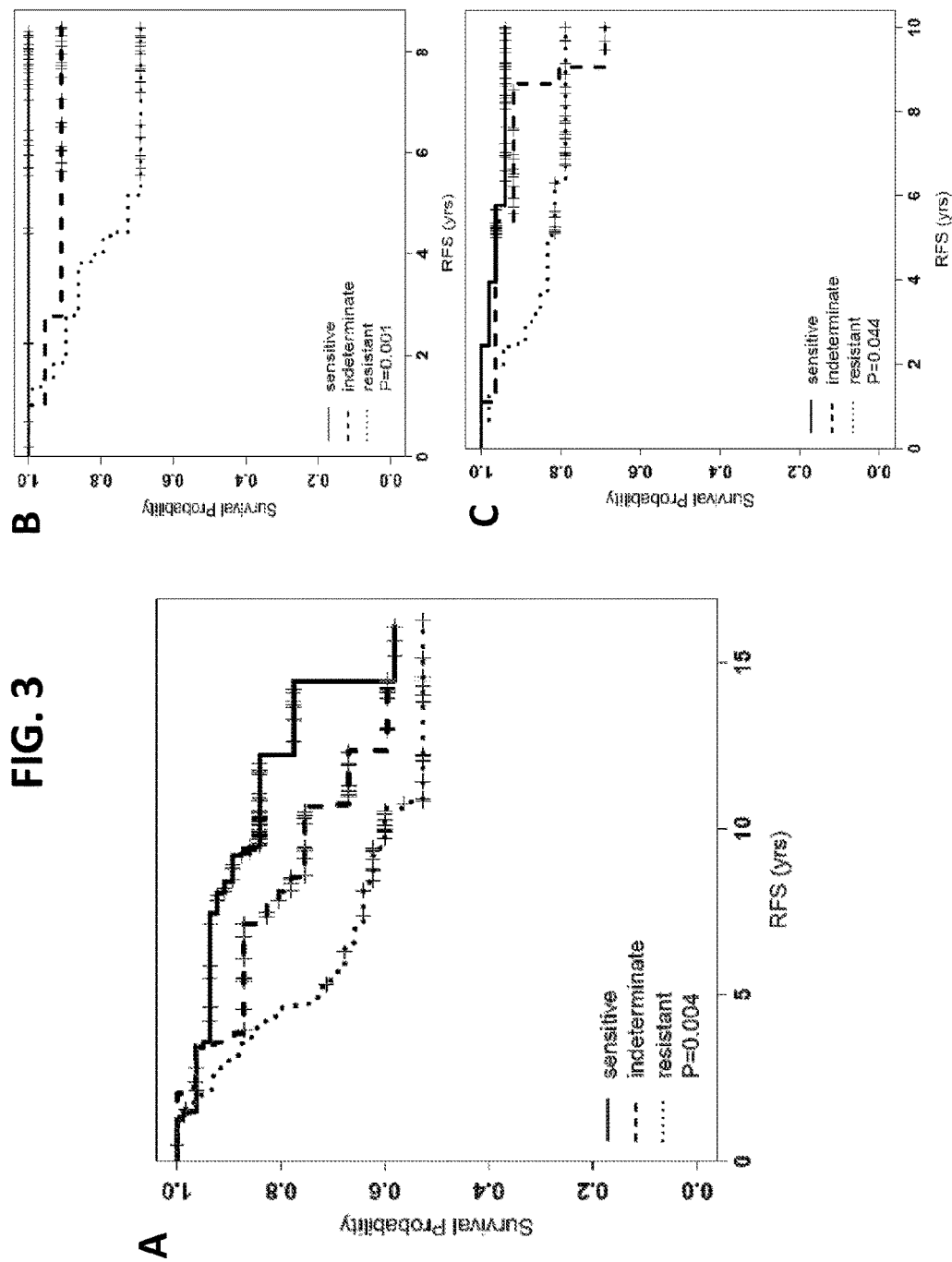
FIG. 3A-C illustrate KM curves of RFS on CADER response groups based on the 54-ERMGs in each of the three public cohorts: Symmans (A), Pawitan (B) and Zhang (C).

A CADER signature through application of a double median cutoff was developed to classify patients into the three groups. Categorical CADER calls (sensitive/indeterminate/resistant) can be separately made on each cohort. The three categories of CADER calls exhibited a balanced distribution on the three public cohorts (Chi-square p-value p=0.48), especially between Symmans and Pawitan (Chi-square p-value p=0.83). The association between CADER and RFS can be tested individually within each cohort. Assembled together, the CADER calls from all the three cohorts can also be tested for a combined association analysis with RFS. The CADER categories successfully produced differing risk of relapse predictions in the combined data (FIG. 2A, Log-rank test P=1.84e-07) as well as within each cohort separately (FIG. 3A-C Log-rank tests, Symmans p=0.004, Pawitan P=0.001, Zhang P=0.044). Survival probabilities (FIG.) of the CADER-sensitive group were nearly 25% higher compared to the resistance group at year 8 (94% vs. 70%) in the combined dataset with an estimated HR (resistant vs. sensitive) of 5.18 (95% CI:2.67~10.08) while the HR of indeterminate to sensitive was 2.31 (95% CI: 1.06~5.02). Kaplan Meier (KM) curves of RFS in the combined public cohorts are displayed in FIG. 2, showing data from all patients (A), the patient subset of intermediate-risk designated by the PAM50 ROR-S model (B), node positive subset of patients (C), and node negative subset of patients (D). CADER groups are indicated as follows: sensitive indicated by solid lines, indeterminate indicated by dashed lines and resistant indicated by dotted lines. The P-values are based on log rank tests. This illustrates that patient stratification into endocrine therapy response groups using the CADER model is significantly associated with survival, even by stratification of node status and within the ROR-S median risk subset.

The CADER assignments were highly concordant with the PAM50 ROR-S (Fisher exact test P=3.50E-44) and the PAM50 intrinsic subtype calls (see Parker, J. S., et al. 2009, referred to herein as "PAM50") (Fisher exact test P=8.22E-37) in the combined dataset and individually (Table 2).

TABLE 2

Concordance between CADER response groups and PAM50-based ROR-S and breast cancer intrinsic subtypes.

| Set | CADER Response Group | N | Node− | Node+ | Node.P |
|---|---|---|---|---|---|
| POL-Z1031 | Sensitive | 86 | | | — |
| | Indeterminate | 53 | | | |
| | Resistant | 92 | | | |
| Loi (N = 263) | Sensitive | 99 | 47 | 48 | 0.5228 |
| | Indeterminate | 69 | 28 | 38 | |
| | Resistant | 95 | 39 | 54 | |
| MDACC (N = 195) | Sensitive | 79 | 52 | 27 | 0.1371 |
| | Indeterminate | 55 | 33 | 22 | |
| | Resistant | 61 | 30 | 31 | |
| Zhang (N = 136) | Sensitive | 54 | 54 | 0 | — |
| | Indeterminate | 28 | 28 | 0 | |
| | Resistant | 54 | 54 | 0 | |
| Pawitan (N = 87) | Sensitive | 35 | 26 | 8 | 0.2592 |
| | Indeterminate | 22 | 11 | 9 | |
| | Resistant | 30 | 20 | 9 | |
| All (N = 418) | Sensitive | 168 | 132 | 35 | 0.1881 |
| | Indeterminate | 105 | 72 | 31 | |
| | Resistant | 145 | 104 | 40 | |

| Set | CADER Response Group | ROR_S Low | Med | High | RORS.P |
|---|---|---|---|---|---|
| POL-Z1031 | Sensitive | 57 | 25 | 0 | 1.73E−23 |
| | Indeterminate | 14 | 32 | 4 | |
| | Resistant | 4 | 55 | 31 | |
| Loi (N = 263) | Sensitive | 47 | 18 | 0 | 3.26E−22 |
| | Indeterminate | 17 | 28 | 4 | |
| | Resistant | 1 | 31 | 30 | |
| MDACC (N = 195) | Sensitive | 67 | 12 | 0 | 1.07E−21 |
| | Indeterminate | 26 | 26 | 3 | |
| | Resistant | 6 | 32 | 23 | |
| Zhang (N = 136) | Sensitive | 45 | 9 | 0 | 2.72E−16 |
| | Indeterminate | 7 | 19 | 2 | |
| | Resistant | 6 | 30 | 18 | |
| Pawitan (N = 87) | Sensitive | 26 | 9 | 0 | 1.85E−11 |
| | Indeterminate | 12 | 10 | 0 | |
| | Resistant | 2 | 11 | 17 | |
| All (N = 418) | Sensitive | 138 | 30 | 0 | 3.50E−44 |
| | Indeterminate | 44 | 55 | 5 | |
| | Resistant | 14 | 73 | 58 | |

| Set | CADER Response Group | Subtype LumA | LumB | Her2 | Basal | Normal | Subtype.P |
|---|---|---|---|---|---|---|---|
| POL-Z1031 | Sensitive | 68 | 18 | | | | 1.16E−22 |
| | Indeterminate | 19 | 34 | | | | |
| | Resistant | 5 | 87 | | | | |
| Loi (N = 263) | Sensitive | 70 | 15 | 2 | 3 | 9 | 1.44E−26 |
| | Indeterminate | 15 | 36 | 3 | 5 | 10 | |
| | Resistant | 2 | 58 | 17 | 14 | 4 | |
| MDACC (N = 195) | Sensitive | 61 | 4 | 0 | 0 | 14 | 2.59E−19 |
| | Indeterminate | 26 | 17 | 1 | 0 | 11 | |
| | Resistant | 10 | 33 | 11 | 6 | 1 | |
| Zhang (N = 136) | Sensitive | 43 | 4 | 0 | 0 | 7 | 2.15E−11 |
| | Indeterminate | 13 | 11 | 0 | 1 | 3 | |
| | Resistant | 10 | 33 | 5 | 3 | 3 | |
| Pawitan (N = 87) | Sensitive | 27 | 6 | 0 | 0 | 2 | 6.21E−08 |
| | Indeterminate | 10 | 8 | 0 | 0 | 4 | |
| | Resistant | 3 | 17 | 5 | 4 | 1 | |

TABLE 2-continued

Concordance between CADER response groups and PAM50-based ROR-S and breast cancer intrinsic subtypes.

| All (N = 418) | Sensitive | 131 | 14 | 0 | 0 | 23 | 8.22E−37 |
|---|---|---|---|---|---|---|---|
| | Indeterminate | 49 | 36 | 1 | 1 | 18 | |
| | Resistant | 23 | 83 | 21 | 13 | 5 | |

Analyzed cohorts include POL-Z1031, Loi, Symmans, Zhang, Pawitan and "All" (combining Symmans, Zhang and Pawitan) in Table 2. High agreement between CADER response groups, ROR-S and breast cancer subtypes can be observed within each individual cohort, as well as the combination of the three public cohorts. The association between CADER classification and RFS was still significant after stratification by nodal status in the combined analysis (FIG. 2C-D, Log rank test P=0.038 in node positive and P=1.82e-05 in node negative). Despite the high concordance with the PAM50-defined groups, the CADER classification stratified the risk of relapse within the subset of patients who were assigned medium risk by the ROR-S model (FIG. 2B, Log rank test P=0.0005). To confirm the independent prognostic ability of CADER, multivariate Cox analysis can be applied. The results (Table 3) show a strong independent prognostic ability of CADER to classic clinical variables (likelihood ratio test P=5.62E-05), with the predicted resistant patients experiencing a HR of 5.32 (95% CI: 2.41~11.76) relative to sensitive patients.

TABLE 3

Multivariate survival analysis of the combined Public cohort (Symmans and Pawitan) for RFS.

| Variable | HR (95% CI) | P |
|---|---|---|
| CADER (N = 238) | | |
| Age (≥65 vs. <65) | 2.4 (1.33~4.35) | 0.0038 |
| Grade (3 vs. 1~2) | 0.62 (0.32~1.19) | 0.1508 |
| Node (Positive vs. Negative) | 2.1 (1.17~3.75) | 0.0126 |
| Tumor Size (≥2.0 cm vs. <2.0 cm) | 2.73 (1.15~6.46) | 0.0227 |
| CADER | | 5.62E-05 |
| indeterminate vs. sensitive | 1.91 (0.81~4.51) | 0.138 |
| resistant vs. sensitive | 5.32 (2.41~11.76) | 3.59E-05 |
| Harrell's C-index | 0.7851 | |
| ROR-S (N = 238) | | |
| Age (≥65 vs. <65) | 2.11 (1.15~3.87) | 0.016 |
| Grade (3 vs. 1~2) | 0.92 (0.47~1.8) | 0.8054 |
| Node (Positive vs. Negative) | 2.52 (1.42~4.48) | 0.0015 |
| Tumor Size (3 vs. 1~2) | 2.59 (1.12~5.98) | 0.0263 |
| ROR_S | | 0.1104 |
| med vs. low | 1.84 (0.99~3.4) | 0.0537 |
| high vs. low | 1.94 (0.83~4.55) | 0.1283 |
| Harrell's C-index | 0.7252 | |
| CADER + ROR-S (N = 238) | | |
| Age (≥65 vs. <65) | 2.27 (1.24~4.15) | 0.0078 |
| Grade (3 vs. 1~2) | 0.66 (0.34~1.31) | 0.2349 |
| Node (Positive vs. Negative) | 2.1 (1.17~3.77) | 0.0132 |
| Tumor Size (≥2.0 cm vs. <2.0 cm) | 2.78 (1.17~6.6) | 0.0201 |
| | | 0.6284 |
| ROR_S | 0.9 (0.44~1.81) | 0.765 |
| med vs. low | 0.64 (0.25~1.64) | 0.3498 |
| high vs. low | | 0.0002 |
| CADER | 2 (0.82~4.86) | 0.1279 |
| indeterminate vs. sensitive | 6.31 (2.51~15.9) | 9.23E-05 |
| resistant vs. sensitive | | |
| Harrell's C-index | 0.7857 | |

TABLE 4

Survival Probability estimation of CADER and ROR-S in Public cohorts.

| Set | CADER | 5 yr survival prob. | 10 yr survival prob. (8 yr for all cohort) |
|---|---|---|---|
| All cohort | sensitive (N = 168) | 0.96 (0.93-0.99) | 0.94 (0.91-0.98) |
| (Symmans, Zhang, Pawitan) | indeterminate (N = 105) | 0.90 (0.85-0.96) | 0.85 (0.78-0.93) |
| | resistant (N = 145 | 0.77 (0.7-0.84) | 0.7 (0.63-0.78) |

| CADER | ROR S | 5 yr survival prob. | 10 yr survival prob. (8 yr for all cohort) |
|---|---|---|---|
| sensitive (N = 168) | low (N = 63) | 0.94 (0.91-0.98) | 0.91 (0.87-0.95) |
| indeterminate (N = 105) | med (N = 197) | 0.85 (0.80-0.91) | 0.79 (0.73-0.86) |
| resistant (N = 145) | high (N = 158) | 0.74 (0.64-0.86) | 0.73 (0.62-0.85) |

When both CADER and ROR-S were included in the multivariate model, CADER remained significant (likelihood ratio test P-value=0.0002) but ROR-S did not. These results illustrate the prognostic effect of CADER response groups is independent of classic clinical variables and ROR-S.

Example 3

This example illustrates a single sample predictor.

A single sample predictor for CADER classification can proceed as the following. Patient can provide a breast cancer tissue sample. The sample can be subject to measurement of the microarray gene expression on the 54 CADER genes using either the Agilent 4*44 K platform or the NanoString nCounter platform. Next, the patient's 54 CADER genes' expression values (along with other patients') can be scaled to have similar distribution as the matching prototype dataset by using the "distance-weighted-discrimination-single sample predictor (DWD-SSP)" tool (for example, Benito, M., et al, Bioinformatics, 2004, 20, 105-114.) or other software developed for this purpose. Then, the patient's gene expression data can be adjusted toward the prototype data, and the patient can be assigned to the one of the three groups based on the nearest neighbor principle. More specifically a patient in each of the three groups in the prototype dataset can be represented as a coordinate in a quadrant in a 2-dimensional space by the resistant and the sensitive gene centroid (FIG. 4). Subsequently, the Euclidean distance of the new patient's gene expression data can be compared to the gene centroid of each of the three groups. The patient can then be assigned to the group with the shortest distance.

Example 4

This example illustrates the complex interplay between gene expression, gene copy and prognostic effects.

Figure 5:
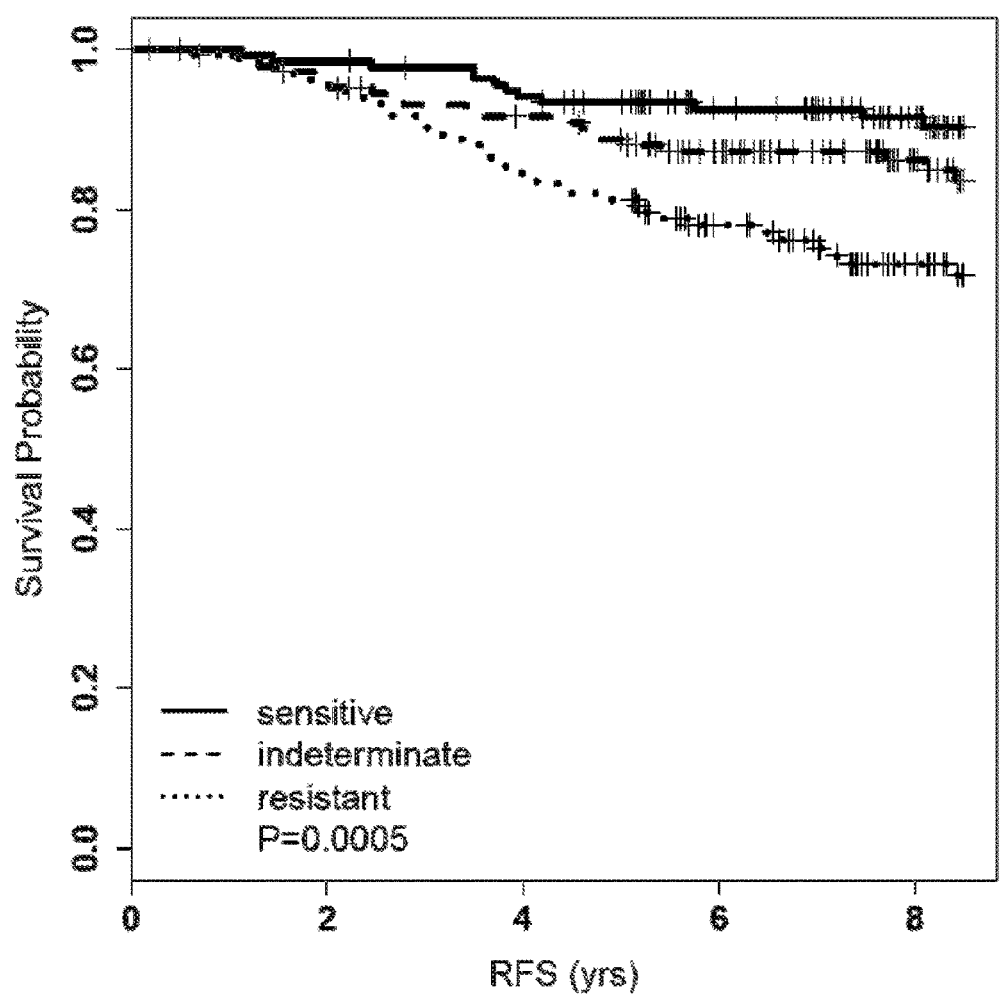
FIG. 5 illustrates KM curves for sensitive/indeterminate/resistance groups using eighteen chromosome 8q resistance genes and six chromosome 8p sensitivity genes.

Examination of Chromosome 8 (Chr8) can show the complex interplay between gene expression, gene copy and prognostic effects. Multiple Chr8 genes were identified as ERMGs. Loss of a large portion of Chr8p and gene copy gain of both the remaining fragment of Chr8p and often concomitant gain of the entire Chr8q arm had a strong influence on gene expression and prognosis. A CADER classification focused only on 24 Chr8 ERMGs in the public data sets produced significant risk stratification in the merged data (FIG. 5, log-rank P=0.005). Notably neither the 21 gene recurrence score (Paik, S., et al. 2004) nor the PAM50 model (Parker, J. S., et al. 2009) includes genes on Chr8. The CADER gene expression signature can successfully parse this complexity and can translate the information into a prognostic test.

Example 5

This example illustrates a patient classified in the indeterminate group using the PAM50 study can be better characterized using the CADER gene expression signature of the present teachings.

In this example, a patient was diagnosed at age 69 as grade 1 node negative with a tumor size of 1.2 cm. Gene expression profile of patient's CADER gene signature is presented in table 5.

TABLE 5

| Endocrine Therapy Sensitivity Genes | | Endocrine Therapy Resistance Genes | |
|---|---|---|---|
| Gene Symbol | Expression Level | Gene Symbol | Expression Level |
| PARP3 | 9.089031301 | CENPE | 5.714622364 |
| AZGP1 | 11.35771279 | CCNB1 | 8.154402347 |
| EPHX2 | 9.070143362 | KIFC1 | 6.484647472 |
| IGFBP4 | 12.32944125 | CCT6A | 9.620321527 |
| NUDT18 | 8.382194264 | EIF2C2 | 8.044701081 |
| FMO5 | 8.142263278 | RAD54B | 5.756407083 |
| C1orf66 | 9.247242841 | VDAC2 | 11.7508889 |
| COL14A1 | 7.416577951 | MCM10 | 6.069573765 |
| PLAT | 9.831019817 | ZWINT | 9.805901534 |
| PCM1 | 11.28875579 | KIF18A | 6.147591126 |
| ZBTB20 | 9.688345972 | RACGAP1 | 8.457413969 |
| NKFB1 | 9.990544209 | TDG | 9.108421015 |
| TK2 | 8.328267011 | NUP107 | 9.937813942 |
| ABAT | 10.16352859 | TMPO | 8.183558895 |
| ACP6 | 10.39248656 | XPOT | 9.450319913 |
| TSPAN7 | 8.854489277 | BIRC5 | 8.129717848 |
| TNFRSF10B | 7.479798286 | TOP2A | 8.069509653 |
| GSTM1 | 10.09219086 | DSC2 | 6.432188782 |
| OSBPL1A | 10.03427376 | EIF2S2 | 7.637794024 |
| KCTD9 | 7.904455623 | UBE2C | 9.62721325 |
| EVL | 12.75017457 | TPX2 | 8.319388569 |
| MAP2K4 | 9.256905695 | C20orf24 | 11.46484768 |
| RPL21 | 13.97244515 | KIF4A | 7.598866178 |
| STC2 | 12.7561502 | | |

*missing gene symbols are ZNF18, PHYHD1, CHDH, which are sensitivity genes, and CDC2, CDCA5, C8orf76, FBXO45, which are resistance genes. These probes were not included in the PAM50 study.

Analyzing the data with the methods of the present teachings, categorizes this patient as low risk. This patient exhibited a relapse-free survival time of 10.22 years.

Example 6

This example illustrates a patient classified in the indeterminate group using the PAM50 study can be better characterized using the CADER gene expression signature of the present teachings.

In this example, patient was diagnosed at age 78 as grade 2 node positive. Gene expression profile of patient's CADER gene signature is presented in table 6.

TABLE 6

| Endocrine Therapy Sensitivity Genes | | Endocrine Therapy Resistance Genes | |
|---|---|---|---|
| Gene Symbol | Expression Level | Gene Symbol | Expression Level |
| PARP3 | 7.706061643 | CENPE | 5.047042347 |
| AZGP1 | 12.80261593 | CCNB1 | 9.559859894 |
| EPHX2 | 4.993816896 | KIFC1 | 6.711240139 |
| IGFBP4 | 10.79447333 | CCT6A | 9.205403494 |
| NUDT18 | 9.07085503 | EIF2C2 | 8.538651152 |
| FMO5 | 7.532417562 | RAD54B | 4.523797903 |
| C1orf66 | 8.820325116 | VDAC2 | 12.01035138 |
| COL14A1 | 6.679366713 | MCM10 | 5.446321834 |
| PLAT | 11.65087922 | ZWINT | 11.22262799 |
| PCM1 | 11.07051999 | KIF18A | 3.237846496 |
| ZBTB20 | 8.711204359 | RACGAP1 | 9.157539202 |
| NKFB1 | 11.27566382 | TDG | 8.564709433 |
| TK2 | 9.063859097 | NUP107 | 9.936110469 |
| ABAT | 9.086053214 | TMPO | 8.40781558 |
| ACP6 | 9.703784979 | XPOT | 8.679222508 |
| TSPAN7 | 9.435145555 | BIRC5 | 8.666361558 |
| TNFRSF10B | 5.94832483 | TOP2A | 8.640228015 |
| GSTM1 | 9.75245794 | DSC2 | 7.280523855 |
| OSBPL1A | 9.601367587 | EIF2S2 | 8.042112414 |
| KCTD9 | 7.885565166 | UBE2C | 10.55005182 |
| EVL | 12.93028836 | TPX2 | 9.792737142 |
| MAP2K4 | 10.1175172 | C20orf24 | 11.34355343 |
| RPL21 | 15.49653705 | KIF4A | 8.988270499 |
| STC2 | 11.67771198 | | |

*missing gene symbols are ZNF18, PHYHD1, CHDH, which are sensitivity genes, and CDC2, CDCA5, C8orf76, FBXO45, which are resistance genes. These probes were not included in the PAM50 study.

Analyzing the data with the methods of the present teachings, categorizes this patient as low risk. This patient exhibited a relapse-free survival time of 13.28 years.

Example 7

This example illustrates a patient classified in the indeterminate group using the PAM50 study can be better characterized using the CADER gene expression signature of the present teachings.

In this example, patient was diagnosed at age 82.6 as grade 1 node negative with a tumor size of 2.5 cm. Gene expression profile of patient's CADER gene signature is presented in table 7.

TABLE 7

| Endocrine Therapy Sensitivity Genes | | Endocrine Therapy Resistance Genes | |
|---|---|---|---|
| Gene Symbol | Expression Level | Gene Symbol | Expression Level |
| PARP3 | 8.174546595 | CENPE | 5.183835158 |
| AZGP1 | 13.16491313 | CCNB1 | 9.329909721 |
| EPHX2 | 8.94232765 | KIFC1 | 8.159754674 |
| IGFBP4 | 10.73512082 | CCT6A | 10.11615574 |
| NUDT18 | 7.614608355 | EIF2C2 | 6.716000941 |
| FMO5 | 9.016646233 | RAD54B | 6.687388038 |
| C1orf66 | 9.343330199 | VDAC2 | 12.02040261 |
| COL14A1 | 5.412112391 | MCM10 | 4.450809873 |
| PLAT | 9.611437635 | ZWINT | 10.05941182 |
| PCM1 | 11.00268588 | KIF18A | 6.517618437 |
| ZBTB20 | 8.412640663 | RACGAP1 | 9.053757653 |
| NKFB1 | 10.31368648 | TDG | 8.283186412 |
| TK2 | 9.063293162 | NUP107 | 10.06027055 |
| ABAT | 11.24702673 | TMPO | 8.534868246 |
| ACP6 | 10.6358907 | XPOT | 8.725274164 |
| TSPAN7 | 7.772079521 | BIRC5 | 8.690569453 |
| TNFRSF10B | 7.675838903 | TOP2A | 9.108931542 |
| GSTM1 | 9.794034203 | DSC2 | 5.869174656 |
| OSBPL1A | 9.989288869 | EIF2S2 | 8.030215231 |
| KCTD9 | 8.509371583 | UBE2C | 9.983460223 |
| EVL | 12.56118174 | TPX2 | 9.441747358 |

TABLE 7-continued

| Endocrine Therapy Sensitivity Genes | | Endocrine Therapy Resistance Genes | |
|---|---|---|---|
| Gene Symbol | Expression Level | Gene Symbol | Expression Level |
| MAP2K4 | 10.41218633 | C20orf24 | 11.19135574 |
| RPL21 | 15.08960134 | KIF4A | 9.086006485 |
| STC2 | 10.7705123 | | |

*missing gene symbols are ZNF18, PHYHD1, CHDH, which are sensitivity genes, and CDC2, CDCA5, C8orf76, FBXO45, which are resistance genes. These probes were not included in the PAM50 study.

Analyzing the data with the methods of the present teachings, categorizes this patient as low risk.
This patient exhibited a relapse-free survival time of 4.62 years.

Example 8

This example illustrates a patient classified in the indeterminate group using the PAM50 study can be better characterized using the CADER gene expression signature of the present teachings.

In this example, patient was diagnosed at age 50 as grade 1 node negative with a tumor size of 2 cm. Gene expression profile of patient's CADER gene signature is presented in table 8.

TABLE 8

| Endocrine Therapy Sensitivity Genes | | Endocrine Therapy Resistance Genes | |
|---|---|---|---|
| Gene Symbol | Expression Level | Gene Symbol | Expression Level |
| PARP3 | 8.423019389 | CENPE | 5.208923128 |
| AZGP1 | 12.14689386 | CCNB1 | 9.067919062 |
| EPHX2 | 7.179973326 | KIFC1 | 7.803930949 |
| IGFBP4 | 10.96270429 | CCT6A | 10.10034748 |
| NUDT18 | 8.093034532 | EIF2C2 | 8.355983071 |
| FMO5 | 8.509914885 | RAD54B | 5.578315416 |
| C1orf66 | 9.268922232 | VDAC2 | 11.98112025 |
| COL14A1 | 7.402107354 | MCM10 | 5.096041201 |
| PLAT | 10.2412839 | ZWINT | 9.400614412 |
| PCM1 | 10.80954268 | KIF18A | 4.320711476 |
| ZBTB20 | 8.216998421 | RACGAP1 | 8.426501711 |
| NKFB1 | 10.37867582 | TDG | 8.424581655 |
| TK2 | 8.642152449 | NUP107 | 10.34239592 |
| ABAT | 10.99556805 | TMPO | 8.238047033 |
| ACP6 | 9.716986412 | XPOT | 9.722447929 |
| TSPAN7 | 8.5971143 | BIRC5 | 8.154255818 |
| TNFRSF10B | 7.789496624 | TOP2A | 8.426551678 |
| GSTM1 | 9.07138847 | DSC2 | 7.916892991 |
| OSBPL1A | 9.709580369 | EIF2S2 | 8.062037251 |
| KCTD9 | 8.12069555 | UBE2C | 9.351723036 |
| EVL | 11.57919319 | TPX2 | 8.857336669 |
| MAP2K4 | 9.476622768 | C20orf24 | 11.54843739 |
| RPL21 | 14.8847084 | KIF4A | 7.999559725 |
| STC2 | 11.89892093 | | |

*missing gene symbols are ZNF18, PHYHD1, CHDH, which are sensitivity genes, and CDC2, CDCA5, C8orf76, FBXO45, which are resistance genes. These probes were not included in the PAM50 study.

Analyzing the data with the methods of the present teachings, categorizes this patient as low risk.
This patient exhibited a relapse-free survival time of 9.48 years.

Example 9

This example illustrates a patient classified in the indeterminate group using the PAM50 study can be better characterized using the CADER gene expression signature of the present teachings.

In this example, patient was diagnosed at age 72 as grade 2 node negative with a tumor size of 2.5 cm. Gene expression profile of patient's CADER gene signature is presented in table 9.

TABLE 9

| Endocrine Therapy Sensitivity Genes | | Endocrine Therapy Resistance Genes | |
|---|---|---|---|
| Gene Symbol | Expression Level | Gene Symbol | Expression Level |
| PARP3 | 8.771670864 | CENPE | 3.651962054 |
| AZGP1 | 14.12907741 | CCNB1 | 8.842648054 |
| EPHX2 | 8.224530958 | KIFC1 | 9.934962727 |
| IGFBP4 | 13.25201221 | CCT6A | 8.541236904 |
| NUDT18 | 9.132402527 | EIF2C2 | 7.812369431 |
| FMO5 | 8.573554651 | RAD54B | 3.771356866 |
| C1orf66 | 10.38687407 | VDAC2 | 11.48336871 |
| COL14A1 | 6.226066377 | MCM10 | 6.289920626 |
| PLAT | 9.894345609 | ZWINT | 9.856885203 |
| PCM1 | 6.610539309 | KIF18A | 4.323664316 |
| ZBTB20 | 9.658834161 | RACGAP1 | 8.678725078 |
| NKFB1 | 9.515187228 | TDG | 8.78362627 |
| TK2 | 9.00909589 | NUP107 | 9.291523701 |
| ABAT | 8.774114776 | TMPO | 8.070476677 |
| ACP6 | 10.57558001 | XPOT | 8.035070874 |
| TSPAN7 | 9.544470732 | BIRC5 | 9.867229559 |
| TNFRSF10B | 5.75209336 | TOP2A | 8.268887116 |
| GSTM1 | 10.61241092 | DSC2 | 8.0597748 |
| OSBPL1A | 9.063677782 | EIF2S2 | 7.677085789 |
| KCTD9 | 6.62967452 | UBE2C | 11.33116967 |
| EVL | 12.21472727 | TPX2 | 9.862771273 |
| MAP2K4 | 7.983384073 | C20orf24 | 12.76892279 |
| RPL21 | 13.50547562 | KIF4A | 8.868607027 |
| STC2 | 10.77093214 | | |

*missing gene symbols are ZNF18, PHYHD1, CHDH, which are sensitivity genes, and CDC2, CDCA5, C8orf76, FBXO45, which are resistance genes. These probes were not included in the PAM50 study.

Analyzing the data with the methods of the present teachings, categorizes this patient as low risk.
This patient exhibited a relapse-free survival time of 10.37 years.

Example 10

This example illustrates a patient classified in the indeterminate group using the PAM50 study can be better characterized using the CADER gene expression signature of the present teachings.

In this example, patient was diagnosed at age 60 as grade 1 node negative with a tumor size of 1.5 cm. Gene expression profile of patient's CADER gene signature is presented in the table 10.

TABLE 10

| Endocrine Therapy Sensitivity Genes | | Endocrine Therapy Resistance Genes | |
|---|---|---|---|
| Gene Symbol | Expression Level | Gene Symbol | Expression Level |
| PARP3 | 8.195331371 | CENPE | 5.632172111 |
| AZGP1 | 13.74984022 | CCNB1 | 8.055483336 |
| EPHX2 | 6.696227011 | KIFC1 | 6.489111331 |
| IGFBP4 | 12.09832399 | CCT6A | 10.38135864 |
| NUDT18 | 8.270420346 | EIF2C2 | 8.755586257 |
| FMO5 | 7.021118002 | RAD54B | 6.958867796 |
| C1orf66 | 9.662189619 | VDAC2 | 11.30180572 |
| COL14A1 | 7.293557331 | MCM10 | 5.917221042 |
| PLAT | 9.920697333 | ZWINT | 9.7205269 |
| PCM1 | 10.02811491 | KIF18A | 3.444838554 |
| ZBTB20 | 10.19466269 | RACGAP1 | 8.419747507 |
| NKFB1 | 9.603847806 | TDG | 9.456320243 |
| TK2 | 8.924649251 | NUP107 | 9.984285983 |

TABLE 10-continued

| Endocrine Therapy Sensitivity Genes | | Endocrine Therapy Resistance Genes | |
|---|---|---|---|
| Gene Symbol | Expression Level | Gene Symbol | Expression Level |
| ABAT | 8.896633344 | TMPO | 7.949108266 |
| ACP6 | 9.285473956 | XPOT | 9.54292892 |
| TSPAN7 | 8.695560913 | BIRC5 | 7.063289261 |
| TNFRSF10B | 6.320138873 | TOP2A | 7.086963896 |
| GSTM1 | 9.681219679 | DSC2 | 8.003530478 |
| OSBPL1A | 9.970328855 | EIF2S2 | 7.436955491 |
| KCTD9 | 7.911145356 | UBE2C | 9.291612864 |
| EVL | 12.0387619 | TPX2 | 8.426273521 |
| MAP2K4 | 8.50845927 | C20orf24 | 11.48997945 |
| RPL21 | 14.66438421 | KIF4A | 6.462304872 |
| STC2 | 10.34574607 | | |

*missing gene symbols are ZNF18, PHYHD1, CHDH, which are sensitivity genes, and CDC2, CDCA5, C8orf76, FBXO45, which are resistance genes. These probes were not included in the PAM50 study.

Analyzing the data with the methods of the present teachings, categorizes this patient as low risk.
This patient exhibited a relapse-free survival time of 9.82 years.

Example 11

This example illustrates a patient classified in the indeterminate group using the PAM50 study can be better characterized using the CADER gene expression signature of the present teachings.

In this example, patient was diagnosed at age 76 as grade 2 node negative with a tumor size of 2 cm. Gene expression profile of patient's CADER gene signature is presented in table 11.

TABLE 11

| Endocrine Therapy Sensitivity Genes | | Endocrine Therapy Resistance Genes | |
|---|---|---|---|
| Gene Symbol | Expression Level | Gene Symbol | Expression Level |
| PARP3 | 9.220276473 | CENPE | 4.890147366 |
| AZGP1 | 13.63396186 | CCNB1 | 9.357511666 |
| EPHX2 | 7.63440817 | KIFC1 | 9.213362515 |
| IGFBP4 | 10.90988711 | CCT6A | 8.961784315 |
| NUDT18 | 9.043535413 | EIF2C2 | 8.739433283 |
| FMO5 | 7.432979371 | RAD54B | 6.007633509 |
| C1orf66 | 9.643784067 | VDAC2 | 11.81497055 |
| COL14A1 | 7.599356611 | MCM10 | 6.617340391 |
| PLAT | 11.32894871 | ZWINT | 10.78246017 |
| PCM1 | 7.474273878 | KIF18A | 5.558831023 |
| ZBTB20 | 9.525264933 | RACGAP1 | 8.939562764 |
| NKFB1 | 9.83374884 | TDG | 8.734711926 |
| TK2 | 8.840877327 | NUP107 | 9.38846082 |
| ABAT | 10.29856415 | TMPO | 8.103172514 |
| ACP6 | 10.5667799 | XPOT | 8.466124368 |
| TSPAN7 | 8.74103966 | BIRC5 | 9.011353969 |
| TNFRSF10B | 7.94094245 | TOP2A | 8.059448642 |
| GSTM1 | 11.16294174 | DSC2 | 6.733968514 |
| OSBPL1A | 9.990399182 | EIF2S2 | 7.133801494 |
| KCTD9 | 7.503238991 | UBE2C | 10.34231341 |
| EVL | 9.296777305 | TPX2 | 8.956665888 |
| MAP2K4 | 8.788801129 | C20orf24 | 12.14857435 |
| RPL21 | 13.81407231 | KIF4A | 7.816111893 |
| STC2 | 12.93997443 | | |

*missing gene symbols are ZNF18, PHYHD1, CHDH, which are sensitivity genes, and CDC2, CDCA5, C8orf76, FBXO45, which are resistance genes. These probes were not included in the PAM50 study.

Analyzing the data with the methods of the present teachings, categorizes this patient as low risk.
This patient exhibited a relapse-free survival time of 8.82 years.

Example 12

This example illustrates a patient classified in the indeterminate group using the PAM50 study can be better characterized using the CADER gene expression signature of the present teachings.

In this example, patient was diagnosed at age 71 as grade 2 node negative with a tumor size of 3.8 cm. Gene expression profile of patient's CADER gene signature is presented in table 12.

TABLE 12

| Endocrine Therapy Sensitivity Genes | | Endocrine Therapy Resistance Genes | |
|---|---|---|---|
| Gene Symbol | Expression Level | Gene Symbol | Expression Level |
| PARP3 | 7.225232241 | CENPE | 5.356683467 |
| AZGP1 | 11.10551416 | CCNB1 | 8.69014881 |
| EPHX2 | 7.608820719 | KIFC1 | 6.627439879 |
| IGFBP4 | 10.14052865 | CCT6A | 9.503117742 |
| NUDT18 | 8.790224261 | EIF2C2 | 8.276676063 |
| FMO5 | 8.352492368 | RAD54B | 7.296602326 |
| C1orf66 | 9.095903836 | VDAC2 | 12.07803136 |
| COL14A1 | 6.801220806 | MCM10 | 4.90426628 |
| PLAT | 12.1254784 | ZWINT | 9.963178365 |
| PCM1 | 10.80643214 | KIF18A | 5.297509956 |
| ZBTB20 | 8.655693668 | RACGAP1 | 8.675716832 |
| NKFB1 | 9.950598064 | TDG | 8.856305995 |
| TK2 | 8.142178994 | NUP107 | 9.825879761 |
| ABAT | 12.07425458 | TMPO | 7.898770909 |
| ACP6 | 9.934738407 | XPOT | 9.409422485 |
| TSPAN7 | 8.615270886 | BIRC5 | 7.920768251 |
| TNFRSF10B | 5.930584997 | TOP2A | 8.274852202 |
| GSTM1 | 10.48712907 | DSC2 | 7.740213072 |
| OSBPL1A | 9.748346575 | EIF2S2 | 7.64317594 |
| KCTD9 | 7.917730095 | UBE2C | 9.971378017 |
| EVL | 11.05681921 | TPX2 | 8.827280345 |
| MAP2K4 | 9.304427564 | C20orf24 | 11.53656485 |
| RPL21 | 14.34440973 | KIF4A | 7.655959994 |
| STC2 | 12.86487322 | | |

*missing gene symbols are ZNF18, PHYHD1, CHDH, which are sensitivity genes, and CDC2, CDCA5, C8orf76, FBXO45, which are resistance genes. These probes were not included in the PAM50 study.

Analyzing the data with the methods of the present teachings, categorizes this patient as low risk.
This patient exhibited a relapse-free survival time of 9.77 years.

Example 13

This example illustrates a patient classified in the indeterminate group using the PAM50 study can be better characterized using the CADER gene expression signature of the present teachings.

In this example, patient was diagnosed at age 71 as grade 2 node negative with a tumor size of 1.1 cm. Gene expression profile of patient's CADER gene signature is presented in table 13.

TABLE 13

| Endocrine Therapy Sensitivity Genes | | Endocrine Therapy Resistance Genes | |
|---|---|---|---|
| Gene Symbol | Expression Level | Gene Symbol | Expression Level |
| PARP3 | 9.291704969 | CENPE | 5.382882804 |
| AZGP1 | 12.78955459 | CCNB1 | 8.440426299 |
| EPHX2 | 9.635858316 | KIFC1 | 6.829062874 |
| IGFBP4 | 11.53492614 | CCT6A | 9.324394803 |
| NUDT18 | 8.580021659 | EIF2C2 | 8.891052037 |
| FMO5 | 9.367852626 | RAD54B | 5.385472494 |

TABLE 13-continued

| Endocrine Therapy Sensitivity Genes | | Endocrine Therapy Resistance Genes | |
|---|---|---|---|
| Gene Symbol | Expression Level | Gene Symbol | Expression Level |
| C1orf66 | 9.531665745 | VDAC2 | 11.42239554 |
| COL14A1 | 7.198780142 | MCM10 | 6.408723154 |
| PLAT | 8.965633637 | ZWINT | 10.00026781 |
| PCM1 | 11.73299647 | KIF18A | 3.071083725 |
| ZBTB20 | 9.995356409 | RACGAP1 | 9.064077065 |
| NKFB1 | 10.39137003 | TDG | 8.955158771 |
| TK2 | 8.610248982 | NUP107 | 9.991926076 |
| ABAT | 10.16325203 | TMPO | 8.339618599 |
| ACP6 | 9.899745943 | XPOT | 9.205077535 |
| TSPAN7 | 8.232730392 | BIRC5 | 8.003442603 |
| TNFRSF10B | 8.125270272 | TOP2A | 8.044071277 |
| GSTM1 | 9.57469389 | DSC2 | 5.813682345 |
| OSBPL1A | 9.742077303 | EIF2S2 | 7.924900627 |
| KCTD9 | 8.122019716 | UBE2C | 9.793971887 |
| EVL | 12.81661697 | TPX2 | 8.571855639 |
| MAP2K4 | 8.464554411 | C20orf24 | 11.58041449 |
| RPL21 | 13.78632737 | KIF4A | 7.9808711 |
| STC2 | 9.597783917 | | |

*missing gene symbols are ZNF18, PHYHD1, CHDH, which are sensitivity genes, and CDC2, CDCA5, C8orf76, FBXO45, which are resistance genes. These probes were not included in the PAM50 study.

Analyzing the data with the methods of the present teachings, categorizes this patient as low risk.

This patient exhibited a relapse-free survival time of 11.03 years.

Example 14

This example illustrates a patient classified in the indeterminate group using the PAM50 study can be better characterized using the CADER gene expression signature of the present teachings.

In this example, patient was diagnosed at age 64 as grade 2 node negative with a tumor size of 4 cm. Gene expression profile of patient's CADER gene signature is presented in table 14.

TABLE 14

| Endocrine Therapy Sensitivity Genes | | Endocrine Therapy Resistance Genes | |
|---|---|---|---|
| Gene Symbol | Expression Level | Gene Symbol | Expression Level |
| PARP3 | 8.672237007 | CENPE | 5.698169245 |
| AZGP1 | 10.03974419 | CCNB1 | 8.499274857 |
| EPHX2 | 7.997469912 | KIFC1 | 8.528740811 |
| IGFBP4 | 9.855627665 | CCT6A | 9.52592378 |
| NUDT18 | 8.405623241 | EIF2C2 | 8.373179934 |
| FMO5 | 9.240328855 | RAD54B | 6.843287473 |
| C1orf66 | 8.995817157 | VDAC2 | 11.54992641 |
| COL14A1 | 7.932292908 | MCM10 | 4.90418841 |
| PLAT | 8.852188372 | ZWINT | 10.28260367 |
| PCM1 | 11.08708954 | KIF18A | 6.428181192 |
| ZBTB20 | 9.793639913 | RACGAP1 | 9.049262721 |
| NKFB1 | 9.967037219 | TDG | 9.118005266 |
| TK2 | 8.642951231 | NUP107 | 9.94434022 |
| ABAT | 9.276640765 | TMPO | 8.588766178 |
| ACP6 | 10.29122674 | XPOT | 9.116196563 |
| TSPAN7 | 7.719768947 | BIRC5 | 8.143036369 |
| TNFRSF10B | 7.640641107 | TOP2A | 8.619855173 |
| GSTM1 | 9.281695426 | DSC2 | 7.808699225 |
| OSBPL1A | 10.05216708 | EIF2S2 | 7.959857094 |
| KCTD9 | 8.239843842 | UBE2C | 9.996023676 |
| EVL | 11.57660733 | TPX2 | 8.505614443 |
| MAP2K4 | 8.738524985 | C20orf24 | 11.67011271 |
| RPL21 | 15.28974011 | KIF4A | 7.810522036 |
| STC2 | 11.64642431 | | |

*missing gene symbols are ZNF18, PHYHD1, CHDH, which are sensitivity genes, and CDC2, CDCA5, C8orf76, FBXO45, which are resistance genes. These probes were not included in the PAM50 study.

Analyzing the data with the methods of the present teachings, categorizes this patient as low risk.

This patient exhibited a relapse-free survival time of 9.45 years.

Example 15

This example illustrates a patient classified in the indeterminate group using the PAM50 study can be better characterized using the CADER gene expression signature of the present teachings.

In this example, patient was diagnosed at age 62 as grade 1 node negative with a tumor size of 2 cm. Gene expression profile of patient's CADER gene signature is presented in table 15.

TABLE 15

| Endocrine Therapy Sensitivity Genes | | Endocrine Therapy Resistance Genes | |
|---|---|---|---|
| Gene Symbol | Expression Level | Gene Symbol | Expression Level |
| PARP3 | 7.95404528 | CENPE | 5.889816181 |
| AZGP1 | 12.96281502 | CCNB1 | 8.977058202 |
| EPHX2 | 3.925829388 | KIFC1 | 6.860790579 |
| IGFBP4 | 13.98951479 | CCT6A | 10.07424594 |
| NUDT18 | 7.342338206 | EIF2C2 | 8.819670918 |
| FMO5 | 8.755710391 | RAD54B | 6.850474828 |
| C1orf66 | 8.502083292 | VDAC2 | 10.70361673 |
| COL14A1 | 6.885825359 | MCM10 | 4.556044807 |
| PLAT | 8.958129179 | ZWINT | 9.90352554 |
| PCM1 | 9.263851333 | KIF18A | 2.43819653 |
| ZBTB20 | 8.760094598 | RACGAP1 | 8.91534784 |
| NKFB1 | 9.944393215 | TDG | 9.143939972 |
| TK2 | 8.550001609 | NUP107 | 10.22940838 |
| ABAT | 10.65823825 | TMPO | 8.625364575 |
| ACP6 | 9.717129716 | XPOT | 10.04425538 |
| TSPAN7 | 8.234606874 | BIRC5 | 8.244907696 |
| TNFRSF10B | 6.783398571 | TOP2A | 9.529961049 |
| GSTM1 | 10.27668464 | DSC2 | 7.958312793 |
| OSBPL1A | 11.07866444 | EIF2S2 | 7.901577226 |
| KCTD9 | 7.495327704 | UBE2C | 10.12534313 |
| EVL | 11.12621928 | TPX2 | 9.347041926 |
| MAP2K4 | 8.92875982 | C20orf24 | 12.26651445 |
| RPL21 | 14.3166023 | KIF4A | 7.967112657 |
| STC2 | 14.76346489 | | |

*missing gene symbols are ZNF18, PHYHD1, CHDH, which are sensitivity genes, and CDC2, CDCA5, C8orf76, FBXO45, which are resistance genes. These probes were not included in the PAM50 study.

Analyzing the data with the methods of the present teachings, categorizes this patient as low risk.

This patient exhibited a relapse-free survival time of 9.4 years.

Example 16

This example refers to examples 5-15 of patients that were classified in the indeterminate group using the PAM50 study can be better characterized using the CADER gene expression signature of the present teachings.

In the Symmans dataset, twelve patients were classified as medium risk by PAM50 but low risk by CADER. Relapse free survival was observed in 11 out of the 12 patients that were re-characterized by CADER therefore the present teaching are able to predict relapse free survival.

Example 17

This example illustrates a patient classified in the low risk group using the PAM50 study can be better characterized using the CADER gene expression signature of the present teachings.

In this example, patient was diagnosed at age 61 as grade 2 node negative with a tumor size of 2.2 cm. Gene expression profile of patient's CADER gene signature is presented in table 16.

TABLE 16

| Endocrine Therapy Sensitivity Genes | | Endocrine Therapy Resistance Genes | |
|---|---|---|---|
| Gene Symbol | Expression Level | Gene Symbol | Expression Level |
| PARP3 | 7.744600437 | CENPE | 7.544588013 |
| AZGP1 | 10.66904972 | CCNB1 | 9.47591913 |
| EPHX2 | 4.805292308 | KIFC1 | 9.506767063 |
| IGFBP4 | 11.29608728 | CCT6A | 10.21427538 |
| NUDT18 | 8.002058823 | EIF2C2 | 8.7960344 |
| FMO5 | 6.155200313 | RAD54B | 6.375895604 |
| C1orf66 | 9.333179208 | VDAC2 | 12.00687248 |
| COL14A1 | 6.288615109 | MCM10 | 7.501949976 |
| PLAT | 9.537949138 | ZWINT | 10.95987061 |
| PCM1 | 9.588582125 | KIF18A | 6.051795069 |
| ZBTB20 | 8.790479168 | RACGAP1 | 9.24241408 |
| NKFB1 | 9.725030872 | TDG | 9.575761169 |
| TK2 | 8.531978461 | NUP107 | 10.32938969 |
| ABAT | 8.159354409 | TMPO | 8.790588323 |
| ACP6 | 9.584543206 | XPOT | 10.49669192 |
| TSPAN7 | 8.693409574 | BIRC5 | 9.336064812 |
| TNFRSF10B | 6.091732191 | TOP2A | 9.421322801 |
| GSTM1 | 9.06286858 | DSC2 | 7.776095411 |
| OSBPL1A | 9.151000584 | EIF2S2 | 8.190102297 |
| KCTD9 | 7.87786112 | UBE2C | 10.78982172 |
| EVL | 10.55251978 | TPX2 | 10.15418118 |
| MAP2K4 | 8.27281105 | C20orf24 | 11.90394725 |
| RPL21 | 13.95732984 | KIF4A | 8.570767398 |
| STC2 | 9.01194817 | | |

*missing gene symbols are ZNF18, PHYHD1, CHDH, which are sensitivity genes, and CDC2, CDCA5, C8orf76, FBXO45, which are resistance genes. These probes were not included in the PAM50 study.

Analyzing the data with the methods of the present teachings, categorizes this patient as resistant thus high risk for relapse.

This patient exhibited distant relapse and had survived without distant relapse for 6.98 years.

Example 18

This example illustrates a patient classified in the low risk group using the PAM50 study can be better characterized using the CADER gene expression signature of the present teachings.

In this example, patient was diagnosed at age 53 as grade 2 node positive with a tumor size of 3.5 cm. Gene expression profile of patient's CADER gene signature is presented in table 17.

TABLE 17

| Endocrine Therapy Sensitivity Genes | | Endocrine Therapy Resistance Genes | |
|---|---|---|---|
| Gene Symbol | Expression Level | Gene Symbol | Expression Level |
| PARP3 | 6.804051671 | CENPE | 5.37205207 |
| AZGP1 | 10.39856245 | CCNB1 | 8.991964499 |
| EPHX2 | 5.513231806 | KIFC1 | 6.771636713 |
| IGFBP4 | 11.7797415 | CCT6A | 10.3483913 |
| NUDT18 | 7.862417652 | EIF2C2 | 8.904665998 |
| FMO5 | 5.658509257 | RAD54B | 7.079699025 |
| C1orf66 | 8.564056693 | VDAC2 | 13.68322287 |
| COL14A1 | 8.03407683 | MCM10 | 6.122997443 |
| PLAT | 10.11372685 | ZWINT | 9.949184652 |
| PCM1 | 9.443642359 | KIF18A | 6.485956244 |
| ZBTB20 | 8.531888877 | RACGAP1 | 8.632956402 |
| NKFB1 | 10.66976642 | TDG | 8.135705715 |
| TK2 | 8.928895236 | NUP107 | 10.29069575 |
| ABAT | 8.16839595 | TMPO | 7.526540447 |
| ACP6 | 9.360656124 | XPOT | 9.91958533 |
| TSPAN7 | 8.640596844 | BIRC5 | 7.847795729 |
| TNFRSF10B | 6.051866381 | TOP2A | 8.010053062 |
| GSTM1 | 9.84184812 | DSC2 | 8.152131803 |
| OSBPL1A | 9.022350499 | EIF2S2 | 8.122990969 |
| KCTD9 | 8.251784271 | UBE2C | 10.09858581 |
| EVL | 11.45450604 | TPX2 | 9.211925163 |
| MAP2K4 | 8.798858799 | C20orf24 | 12.24436801 |
| RPL21 | 14.78763383 | KIF4A | 8.680433487 |
| STC2 | 11.53819169 | | |

*missing gene symbols are ZNF18, PHYHD1, CHDH, which are sensitivity genes, and CDC2, CDCA5, C8orf76, FBXO45, which are resistance genes. These probes were not included in the PAM50 study.

Analyzing the data with the methods of the present teachings, categorizes this patient as resistant thus high risk for relapse.

This patient exhibited distant relapse and had survived without distant relapse for 5.22 years.

Example 19

This example illustrates a patient classified in the low risk group using the PAM50 study can be better characterized using the CADER gene expression signature of the present teachings.

In this example, patient was diagnosed at age 68 as grade 1 node positive with a tumor size of 9.9 cm. Gene expression profile of patient's CADER gene signature is presented in table 18.

TABLE 18

| Endocrine Therapy Sensitivity Genes | | Endocrine Therapy Resistance Genes | |
|---|---|---|---|
| Gene Symbol | Expression Level | Gene Symbol | Expression Level |
| PARP3 | 7.941656208 | CENPE | 5.820982523 |
| AZGP1 | 11.91844546 | CCNB1 | 9.080828313 |
| EPHX2 | 11.09221285 | KIFC1 | 8.443053537 |
| IGFBP4 | 11.09921988 | CCT6A | 9.912108147 |
| NUDT18 | 7.291000984 | EIF2C2 | 9.014789327 |
| FMO5 | 5.507258787 | RAD54B | 7.373821752 |
| C1orf66 | 8.052387123 | VDAC2 | 12.24316711 |
| COL14A1 | 6.619255837 | MCM10 | 5.481657234 |
| PLAT | 9.179447346 | ZWINT | 9.928994375 |
| PCM1 | 9.999879743 | KIF18A | 7.056975017 |
| ZBTB20 | 8.664983154 | RACGAP1 | 9.481396294 |
| NKFB1 | 9.962166703 | TDG | 8.90556312 |
| TK2 | 8.363256706 | NUP107 | 10.45249963 |
| ABAT | 8.00208168 | TMPO | 7.768463425 |
| ACP6 | 9.287822071 | XPOT | 9.563085024 |
| TSPAN7 | 8.75268169 | BIRC5 | 8.48871999 |
| TNFRSF10B | 7.582667467 | TOP2A | 9.319611162 |
| GSTM1 | 10.13714896 | DSC2 | 6.847939442 |

TABLE 18-continued

| Endocrine Therapy Sensitivity Genes | | Endocrine Therapy Resistance Genes | |
|---|---|---|---|
| Gene Symbol | Expression Level | Gene Symbol | Expression Level |
| OSBPL1A | 10.21907084 | EIF2S2 | 8.340508305 |
| KCTD9 | 8.544638002 | UBE2C | 9.971599409 |
| EVL | 10.3354868 | TPX2 | 9.405812825 |
| MAP2K4 | 7.800937453 | C20orf24 | 12.00273341 |
| RPL21 | 14.15711663 | KIF4A | 8.013343028 |
| STC2 | 10.27067709 | | |

*missing gene symbols are ZNF18, PHYHD1, CHDH, which are sensitivity genes, and CDC2, CDCA5, C8orf76, FBXO45, which are resistance genes. These probes were not included in the PAM50 study.

Analyzing the data with the methods of the present teachings, categorizes this patient as resistant thus high risk for relapse.

This patient exhibited distant relapse and had survived without distant relapse for 4.66 years.

Example 20

This example illustrates a patient classified in the low risk group using the PAM50 study can be better characterized using the CADER gene expression signature of the present teachings.

In this example, patient was diagnosed at age 66 as grade 2 node negative with a tumor size of 4 cm. Gene expression profile of patient's CADER gene signature is presented in table 19.

TABLE 19

| Endocrine Therapy Sensitivity Genes | | Endocrine Therapy Resistance Genes | |
|---|---|---|---|
| Gene Symbol | Expression Level | Gene Symbol | Expression Level |
| PARP3 | 8.575552586 | CENPE | 5.702899308 |
| AZGP1 | 11.37810078 | CCNB1 | 9.954936246 |
| EPHX2 | 5.625112756 | KIFC1 | 7.746900849 |
| IGFBP4 | 11.49885025 | CCT6A | 9.318846576 |
| NUDT18 | 8.252384776 | EIF2C2 | 9.173067959 |
| FMO5 | 5.640726866 | RAD54B | 6.204679593 |
| C1orf66 | 9.838671483 | VDAC2 | 12.33336871 |
| COL14A1 | 7.175991287 | MCM10 | 4.978675499 |
| PLAT | 11.14152372 | ZWINT | 9.799826718 |
| PCM1 | 8.676624207 | KIF18A | 5.066342911 |
| ZBTB20 | 9.359683135 | RACGAP1 | 9.958406158 |
| NKFB1 | 9.804029895 | TDG | 9.03871544 |
| TK2 | 8.627974937 | NUP107 | 9.704097868 |
| ABAT | 7.87688799 | TMPO | 8.42129297 |
| ACP6 | 10.06691172 | XPOT | 9.736253402 |
| TSPAN7 | 8.465600958 | BIRC5 | 8.988490932 |
| TNFRSF10B | 5.909433537 | TOP2A | 9.10676166 |
| GSTM1 | 12.05894345 | DSC2 | 8.097231854 |
| OSBPL1A | 10.15966192 | EIF2S2 | 8.45169494 |
| KCTD9 | 6.895008503 | UBE2C | 11.9116952 |
| EVL | 12.22035136 | TPX2 | 10.42247756 |
| MAP2K4 | 8.843494166 | C20orf24 | 13.05330118 |
| RPL21 | 14.22740117 | KIF4A | 7.893017097 |
| STC2 | 12.64230526 | | |

*missing gene symbols are ZNF18, PHYHD1, CHDH, which are sensitivity genes, and CDC2, CDCA5, C8orf76, FBXO45, which are resistance genes. These probes were not included in the PAM50 study.

Analyzing the data with the methods of the present teachings, categorizes this patient as resistant thus high risk for relapse.

This patient exhibited distant relapse and had survived without distant relapse for 5.68 years.

Example 21

This example illustrates a patient classified in the low risk group using the PAM50 study can be better characterized using the CADER gene expression signature of the present teachings.

In this example, patient was diagnosed at age 61 as grade 3 node positive with a tumor size of 3 cm. Gene expression profile of patient's CADER gene signature is presented in table 20.

TABLE 20

| Endocrine Therapy Sensitivity Genes | | Endocrine Therapy Resistance Genes | |
|---|---|---|---|
| Gene Symbol | Expression Level | Gene Symbol | Expression Level |
| PARP3 | 7.381832762 | CENPE | 7.085017638 |
| AZGP1 | 10.64694672 | CCNB1 | 8.638235879 |
| EPHX2 | 7.549320403 | KIFC1 | 8.129562479 |
| IGFBP4 | 12.1897795 | CCT6A | 8.923314956 |
| NUDT18 | 7.802321466 | EIF2C2 | 8.834816089 |
| FMO5 | 7.751416609 | RAD54B | 5.881147478 |
| C1orf66 | 8.943595771 | VDAC2 | 11.87057155 |
| COL14A1 | 7.984848322 | MCM10 | 7.072996991 |
| PLAT | 10.83283341 | ZWINT | 9.926258074 |
| PCM1 | 10.86560731 | KIF18A | 5.780102567 |
| ZBTB20 | 10.32743519 | RACGAP1 | 8.843596679 |
| NKFB1 | 10.14861856 | TDG | 9.445600595 |
| TK2 | 8.511326627 | NUP107 | 9.962609964 |
| ABAT | 8.19708022 | TMPO | 8.355612197 |
| ACP6 | 9.416616338 | XPOT | 9.200544014 |
| TSPAN7 | 8.395774951 | BIRC5 | 8.314366606 |
| TNFRSF10B | 7.110230031 | TOP2A | 8.881611607 |
| GSTM1 | 9.235942407 | DSC2 | 7.863153004 |
| OSBPL1A | 9.309367829 | EIF2S2 | 7.712268984 |
| KCTD9 | 7.720045847 | UBE2C | 10.07626817 |
| EVL | 12.13976416 | TPX2 | 8.850223895 |
| MAP2K4 | 8.417635977 | C20orf24 | 12.08210918 |
| RPL21 | 14.25344008 | KIF4A | 8.257021285 |
| STC2 | 8.652446485 | | |

*missing gene symbols are ZNF18, PHYHD1, CHDH, which are sensitivity genes, and CDC2, CDCA5, C8orf76, FBXO45, which are resistance genes. These probes were not included in the PAM50 study.

Analyzing the data with the methods of the present teachings, categorizes this patient as resistant thus high risk for relapse.

This patient exhibited distant relapse and had survived without distant relapse for 10.8 years.

Example 22

This example refers to examples 17-21 of patients that were classified in the low risk group using the PAM50 study can be better characterized using the CADER gene expression signature of the present teachings.

In the Symmans dataset, six patients were classified as low risk for relapse by PAM50 but high risk for relapse by CADER. Distant relapse was observed in 5 out of the 6 patients that were re-characterized by CADER therefore the present teachings are able to predict distant relapse.

All references cited are hereby incorporated by reference, each in its entirety.

What is claimed is:

1. A method of predicting the likelihood of long-term survival without recurrence of cancer for a subject having estrogen receptor positive (ER+) breast cancer treated with endocrine monotherapy, the method comprising:
   a) obtaining a breast cancer tissue sample from a human subject;
   b) generating cDNA from the sample;

c) detecting expression levels of a set of genes consisting of (i) endocrine therapy sensitivity genes PARP3, AZGP1, EPHX2, IGFBP4, NUDT18, FOM5, C1orf66, COL14A1, PLAT, PCM1, ABTB20, NFKB1, TK2, ABAT, ANF18, PHYHD1, and CHDH and (ii) endocrine monotherapy resistance genes CENPE, CCNB1, KIFC1, CCT6A, EIF2C2, RAD54B, VDAC2, MCM10, ZWINT, KIF18A, RACGAP1, TDG, NUP107, TMPO, XPOT, BIRC5, TOP2A, DSC2, EIP2S2, UBEC2C, TPX2, C20orf24, KIF4A, CDC2, CDCA5, C8orf76, and FBXO45 from the cDNA; and d) assigning the subject to a sensitive, indeterminate or resistant group, wherein assignment to the sensitive group predicts longer relapse-free survival compared to the resistant group, wherein the assigning the subject to a sensitive, indeterminate or resistant group comprises determining the gene centroid of the endocrine therapy sensitivity genes and the gene centroid of the endocrine therapy resistance genes.

2. The method of claim 1, wherein the assigning the subject to a sensitive, indeterminate or resistant group comprises representing the expression levels as a coordinate in a quadrant in a 2-dimensional space comprising the resistant gene centroid and the sensitive gene centroid and determining a Euclidean distance of the expression levels to a gene centroid of each of the sensitive, resistant and indeterminate groups, wherein the subject is assigned to the group with the shortest distance.

3. The method of claim 1, wherein the endocrine monotherapy comprises a therapy selected from the group consisting of tamoxifen treatment and aromatase inhibitor treatment.

4. The method of claim 1, further consisting of detecting expression levels of one or more housekeeping genes.

5. The method of claim 4, wherein the one or more housekeeping genes are selected from the group consisting of MRPL19, SF3A1, and PUM1.

6. A The method of claim 4, wherein the one or more housekeeping genes are selected from the group consisting of MRPL19, SF3A1, PUM1, ACTB, GAPD, GUSB, RPLP0, and TFRC.

7. A method of predicting the likelihood of long-term survival without recurrence of cancer for a subject having estrogen receptor positive (ER+) breast cancer treated with endocrine monotherapy, the method comprising:
a) obtaining a breast cancer tissue sample from a human subject;
b) generating cDNA from the sample;
c) detecting expression levels of a set of genes consisting of (i) endocrine therapy sensitivity genes PARP3, AZGP1, EPHX2, IGFBP4, NUDT18, FOM5, C1orf66, COL14A1, PLAT, PCM1, ABTB20, NFKB1, TK2, ABAT, ANF18, PHYHD1, and CHDH and (ii) endocrine monotherapy resistance genes CENPE, CCNB1, KIFC1, CCT6A, EIF2C2, RAD54B, VDAC2, MCM10, ZWINT, KIF18A, RACGAP1, TDG, NUP107, TMPO, XPOT, BIRC5, TOP2A, DSC2, EIP2S2, UBEC2C, TPX2, C20orf24, KIF4A, CDC2, CDCA5, C8orf76, and FBXO45 from the cDNA;

d) scaling the expression levels to have similar distribution of a matching prototype dataset in which patients belong to a sensitive, an indeterminate or a resistant group based on the centroids of the sensitive genes and the resistant genes; and e) assigning the subject to the sensitive, indeterminate or resistant group, wherein assignment to the sensitive group predicts longer relapse-free survival compared to the resistant group, wherein the assigning the subject to a sensitive, indeterminate or resistant group comprises determining the gene centroid of the endocrine therapy sensitivity genes and the gene centroid of the endocrine therapy resistance genes.

8. The method of claim 7, wherein detecting the expression levels comprises performing a quantitative RT-PCR assay.

9. The method of claim 7, further comprising providing a microarray consisting of probes for (i) endocrine therapy sensitivity genes PARP3, AZGP1, EPHX2, IGFBP4, NUDT18, FMO5, C1orf66, COL14A1, PLAT, PCM1, ZBTB20, NFKB1, TK2, ABAT, ACP6, TSPAN7, TNFRSF10B, OSBPL1A, KCTD9, EVL, MAP2K4, RPL21, STC2, ZNF18, PHYHD1, and CHDH, and (ii) endocrine therapy resistance genes CENPE, CCNB1, KIFC1, CCT6A, EIF2C2, RAD54B, VDAC2, MCM10, ZWINT, KIF18A, RACGAP1, TDG, NUP107, TMPO, XPOT, BIRC5, TOP2A, DSC2, EIF2S2, UBE2C, TPX2, C20orf24, KIF4A, CDC2, CDCA5, C8orf76, and FBXO45.

10. The method of claim 7, wherein the assigning the subject to a sensitive, indeterminate or resistant group comprises representing the expression levels as a coordinate in a quadrant in a 2-dimensional space comprising the resistant gene centroid and the sensitive gene centroid and determining a Euclidean distance of the expression levels to a gene centroid of each of the sensitive, resistant and indeterminate groups, wherein the subject is assigned to the group with the shortest distance.

11. The method of claim 7, wherein the endocrine monotherapy comprises a therapy selected from the group consisting of tamoxifen treatment and aromatase inhibitor treatment.

* * * * *